(12) United States Patent
Biju et al.

(10) Patent No.: US 9,902,746 B2
(45) Date of Patent: Feb. 27, 2018

(54) BENZOXAPHOSPHOLE COMPOUNDS AND A PROCESS FOR PREPARATION THEREOF

(71) Applicant: Council of Scientific & Industrial Research, New Delhi (IN)

(72) Inventors: Akkattu Thankappan Biju, Maharashtra (IN); Anup Bhunia, Maharashtra (IN); Trinadh Kaicharla, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/121,330

(22) PCT Filed: Feb. 25, 2015

(86) PCT No.: PCT/IN2015/000105
§ 371 (c)(1),
(2) Date: Aug. 24, 2016

(87) PCT Pub. No.: WO2015/128878
PCT Pub. Date: Sep. 3, 2015

(65) Prior Publication Data
US 2017/0015691 A1    Jan. 19, 2017

(30) Foreign Application Priority Data
Feb. 25, 2014   (IN) .............................. 532/DEL/2014

(51) Int. Cl.
C07F 9/6571   (2006.01)

(52) U.S. Cl.
CPC .............................. *C07F 9/657163* (2013.01)

(58) Field of Classification Search
CPC ................................................. C07F 9/657163
See application file for complete search history.

(56) References Cited

PUBLICATIONS

Hiroto Yoshida, et al.; "Three-Component Coupling of Arynes, Aminosilanes, and Aldehydes"; American Chemical Society; 2017; vol. 9, No. 17; pp. 3367-3370, Organic Letters, 2007.
Emmanuelle Remond, et al.; "Efficient Synthesis of Quaternary and P-Stereogenic Phosphonium Inflates"; American Chemical Society; 2010; vol. 12, No. 7; pp. 1568-1571, Organic Letters.
Hiroto Yoshida, et al.; "Arynes in a Three-Component Coupling of Reaction: Straightforward Synthesis of Benzoannulated Iminofurans"; Angew. Chem. Int. Ed.; 2004; pp. 3935-3938.
Anup Bhunia, et al.; "Multicomponent Reactions Involving Arynes, Quinolines, and Aldehydes"; American Chemical Society; 2013; vol. 15, No. 17; pp. 4620-4623, Organic Letters.
Itshak Granoth, et al.; "Stable Monocyclic Monoalkoxyhalophosphoranes: Possible Examples of Structures on the Borderline Between Haloalkoxyphosphoranes and Alkoxyphosphonium Halides"; American Chemical Society; 1981; pp. 2711-2715.

*Primary Examiner* — Rosalynd A Keys
(74) *Attorney, Agent, or Firm* — Blank Rome LLP

(57) ABSTRACT

The present inventors prepared novel benzoxaphosphole compounds and shown a process for the synthesizing these novel compounds. The process of preparing the compounds is simple, transition metal free and gives product with high yield. The synthesized benzoxaphosphole compounds are expected to show potential biological.

9 Claims, No Drawings

BENZOXAPHOSPHOLE COMPOUNDS AND A PROCESS FOR PREPARATION THEREOF

FIELD OF THE INVENTION

The present invention relates to novel benzoxaphosphole compounds of formula (I). More particularly, the present invention relates to novel benzoxaphosphole compounds of formula (I) and process for preparation thereof.

BACKGROUND AND PRIOR ART

Multicomponent Reactions (MCRs) are one-pot reactions, in which three or more starting materials react to form a product, where basically all or most of the atoms contribute to the newly formed product. Speed, diversity, efficiency, atom-economy and environmental friendliness are some of the notable features of this class of reactions. The most important MCRs are the isocyanide-based reactions such as the Passerini three-component reaction and the Ugi four-component reaction. Moreover, a variety of heterocycles can be constructed using the MCR strategy, where zwitterionic intermediates are generated by the addition of nucleophile to activated C—C multiple bonds followed by their interception with a third component.

Arynes are highly electrophilic reactive intermediates, which have been extensively utilized in various carbon-carbon and carbon-heteroatom bond-forming reactions. One of the important aspects of aryne chemistry is multicomponent reaction, which mainly include the initial addition of nucleophiles to arynes and subsequent trapping of the aryl anion intermediate with electrophiles. If the nucleophile and electrophile do not belong to the same molecule, the overall process is a unique three-component coupling, where the aryne is inserted between the other two coupling partners (eqn (1)). This versatile transition-metal-free methodology has been applied to the synthesis of valuable heterocycles and in natural product synthesis.

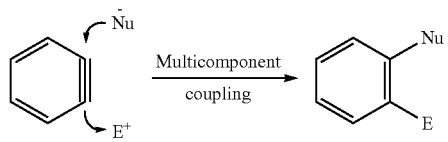

(1)

Organophosphorus compounds are highly effective insecticides and widely used in synthetic organic chemistry. Some of the common applications include the use of phosphonium ylides in the Wittig reaction, the use of phosphines in the Staudinger and Mitsunobu reactions, and the use of phosphines as ligands in transition metal-mediated processes. Phosphorus and nitrogen are in group 5 in periodic table, and thus both the compounds have many similar properties. Generally organophosphorus compounds are based on the two oxidation sate of phosphorus e.g., phosphorus (V) vs phosphorus (III). Commonly organophosphorous compounds contain C—P bond (excluding phosphate and phosphate esters, which lack this kind of bonding).

In the last decade there are significant developments in aryne based MCR process. Some of the benzoxaphospholes are known to possess anti-oxidant activity. Several phosphorus-containing compounds are known to be potential insecticides, bactericides, fungicides, and antibiotic reagents, because of their biological activities, and such compounds exist widely in nature. In addition, oxaphosphole-based monophosphorus compounds are known to be excellent ligands for palladium-catalyzed amination reactions.

U.S. Pat. No. 4,250,320 discloses a process for the production of substituted benzoxaphospholes which are useful as herbicides. The substituted benzoxaphospholes are:

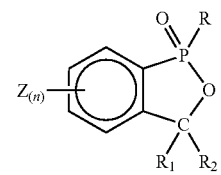

wherein R is selected from the group consisting of lower alkyl, lower alkoxy, $C_3$-$C_8$ cycloalkyl, phenyl, biphenyl, phenoxyphenyl and substituted phenyl containing from one to three substituents individually selected from the class consisting of lower alkyl, lower alkoxy, lower dialkylamino, diphenylamino, $C_3$-$C_8$ cycloalkyl, fluoro, chloro, trifluoromethyl and trimethylsilyl; $R_1$ and $R_2$ are independently selected from the group consisting of hydrogen, lower alkyl, $C_3$-$C_8$ cycloalkyl, and phenyl; Z is selected from the group consisting of lower alkyl, lower alkoxy, phenyl, phenoxy, lower dialkylamino, diphenylamino, $C_3$-$C_8$ cycloalkyl, fluoro, chloro, trifluoromethyl and trimethylsilyl; n is an integer from 0 to 2.

US4219510 discloses novel substituted benzoxaphospholes which are useful as herbicides. The novel substituted benzoxaphospholes are:

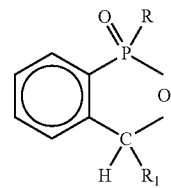

wherein;
R is selected from the group consisting of hydroxy, lower alkyl, lower alkoxy, phenyl and haloalkyl phenyl; and $R_1$ is selected from the group consisting of hydrogen and lower alkyl.

Article titled "Three-component coupling of arynes, aminosilanes, and aldehydes" by Hiroto Yoshida et al. published in Organic Letters, 2007, 9 (17), pp 3367-3370 reports a three-component coupling of arynes, aminosilanes and aldehydes enables diverse amino and hydroxymethyl groups to be incorporated directly into 1,2-positions of aromatic rings. The reaction carried out in presence of KF and 18-Crown-6 in THF solvent.

Article titled "Efficient synthesis of quaternary and p-stereogenic phosphonium triflates" by E Remond et al published in Org. Lett., 2010, 12 (7), pp 1568-1571 reports an efficient and general method for the preparation of achiral and chiral phosphonium salts. This synthesis is based on the quaternization of phosphines and their compounds with arynes generated in situ from 2-(trimethylsilyl)aryl triflates. This methodology is successfully applied to the synthesis of new valuable P-stereogenic phosphonium triflates.

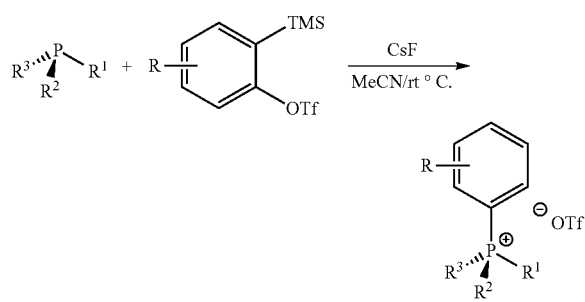

18 examples 58-95%
R^1-3 = H, alkyl, aryl, amino groups

Article titled "Arynes in a Three-Component Coupling Reaction: Straightforward Synthesis of Benzoannulated Iminofurans" by hiroto Yoshida et al. published in *Angewandte Chemie International Edition*, 2004, 43 (30), pages 3935-3938 reports a variety of benzoannulated iminofurans obtained from an aryne, an isocyanide, and aldehyde in modest to high yields.

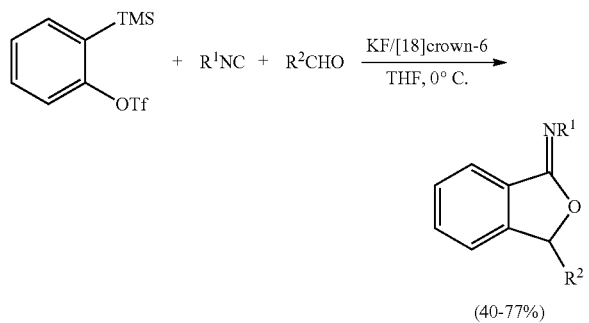

$R^1$ = alkyl; $R^2$ = aryl, alkyl

Article titled "Multicomponent reactions involving arynes, quinolines, and aldehydes" by A Bhunia et al. published in Org. Lett., 2013, 15 (17), pp 4620-4623 reports the multicomponent reaction involving arynes, quinolines, and aldehydes leading to the diastereoselective synthesis of benzoxazino quinoline compounds in good yields proceeding via 1,4-zwitterionic intermediates. In addition, the synthetic potential of various carbonyl compounds in this reaction as well as the utility of isoquinoline as the nucleophilic trigger has been examined.

Multicomponent reaction using aryne is known, but utilizing phosphine as the nucleophilic trigger is very rare. Although nucleophilic phosphine-catalysis is a powerful tool for the construction of various carbocycles and heterocycles, the reactions where phosphines are incorporated in the final product are rare, and the reports on phosphine addition to highly electrophilic arynes are scarce. Interestingly, however, the utility of the phosphine as a substrate, which is incorporated in the final product thus constituting multicomponent reactions (MCRs) are not well-explored compared to nucleophilic phosphine catalysis The inventors developed the phosphine triggered multicomponent reaction of arynes and aldehydes, which takes place via the formal [3+2] cycloaddition of initially generated 1,3-phosphonium zwitterion from phosphine and aryne with aldehydes, wherein the process is transition-metal free and the said multicomponent reaction afford high yield and selectivity of stable pentacovalent phosphoranes based on the benzooxaphosphole system.

OBJECTS OF THE INVENTION

The main object of the present invention is to provide novel benzoxaphosphole compounds of formula (I).

Another object of the present invention is to provide novel benzoxaphosphole compounds which are expected to show some potential biological activities.

Another object of the present invention is to provide a process for the preparation of novel benzoxaphosphole compounds of formula (I) wherein phosphine is treated with aryne and aldehyde to give complex dihydro-benzo-oxaphosphole compounds.

Another object of the present invention is provide a process which is simple, transition metal free and gives product with high yield.

SUMMARY OF THE INVENTION

The present invention provides a compound of formula (I),

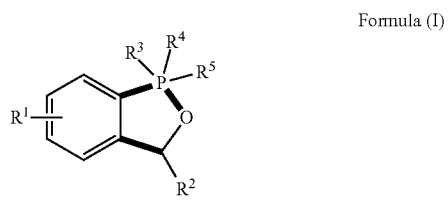

Formula (I)

Wherein, $R^1$ is selected from hydrogen, alkyl, halogen, OMe, —OCH$_2$O—, —(CH$_2$)$_3$—, —(CH$_2$)$_4$— naphthyl, phenanthryl;

$R^2$ is selected from various aromatic aldehydes (electron releasing, electron withdrawing and neutral), aliphatic aldehydes, heterocyclic aldehydes, α,β-unsaturated aldehydes; and $R^3$, $R^4$, $R^5$ are independently selected from aryl, heteroaryl, alkyl phosphines.

In an embodiment of the present invention the compounds of formula (I) are preferably selected from group comprising
3-(4-Chlorophenyl)-1,1,1-triphenyl-1,3-dihydro-1λ$^5$-benzo [c][1,2]oxaphosphole (4a),
3-(4-Methoxyphenyl)-1,1,1-triphenyl-1,3-dihydro-1λ$^5$-benzo[c][1,2]oxaphosphole (4b),
1,1,1-Triphenyl-3-(p-tolyl)-1,3-dihydro-1λ$^5$-benzo[c][1,2] oxaphosphole (4c),
3-(4-Bromophenyl)-1,1,1-triphenyl-1,3-dihydro-1λ$^5$-benzo [c][1,2]oxaphosphole (4d),
1,1,1,3-Tetraphenyl-1,3-dihydro-1λ$^5$-benzo[c][1,2] oxaphosphole (4e),
3-(4-Fluorophenyl)-1,1,1-triphenyl-1,3-dihydro-1λ$^5$-benzo [c][1,2]oxaphosphole (4f),
1,1,1-Triphenyl-3-(4-(trifluoromethyl)phenyl)-1,3-dihydro-1λ$^5$-benzo[c][1,2] oxaphosphole (4g),
Methyl-4-(1,1,1-triphenyl-1,3-dihydro-1λ$^5$-benzo[c][1,2] oxaphosphol-3-yl) benzoate (4h),
4-(1,1,1-Triphenyl-1,3-dihydro-1λ$^5$-benzo[c][1,2] oxaphosphol-3-yl)benzonitrile (4i),
3-(3-Methoxyphenyl)-1,1,1-triphenyl-1,3-dihydro-1λ$^5$-benzo [c][1,2]oxaphosphole (4j),
3-(3-Bromophenyl)-1,1,1-triphenyl-1,3-dihydro-1λ$^5$-benzo [c][1,2]oxaphosphole (4k), 3-(3-Nitrophenyl)-1,1,1-triphenyl-1,3-dihydro-1λ$^5$-benzo[c][1,2]oxaphosphole (4l),
1,1,1-Triphenyl-3-(o-tolyl)-1,3-dihydro-1λ$^5$-benzo[c][1,2]oxaphosphole (4m),
3-(2-Fluorophenyl)-1,1,1-triphenyl-1,3-dihydro-1λ$^5$-benzo[c][1,2]oxaphosphole (4n),
3-(3,4-Dichlorophenyl)-1,1,1-triphenyl-1,3-dihydro-1λ$^5$-benzo[c][1,2]oxaphosphole (4o),
3-Mesityl-1,1,1-triphenyl-1,3-dihydro-1λ$^5$-benzo[c][1,2]oxaphosphole (4p),
3-(Naphthalen-2-yl)-1,1,1-triphenyl-1,3-dihydro-1λ$^5$-benzo[c][1,2]oxaphosphole (4q),
1,1,1-Triphenyl-3-(pyren-4-yl)-1,3-dihydro-1λ$^5$-benzo[c][1,2]oxaphosphole (4r),
3-(Benzofuran-2-yl)-1,1,1-triphenyl-1,3-dihydro-1λ$^5$-benzo[c][1,2]oxaphosphole (4s),
1,1,1-Triphenyl-3-(thiophen-2-yl)-1,3-dihydro-1λ$^5$-benzo[c][1,2] oxaphosphole (4t),
3-Cyclohexyl-1,1,1-triphenyl-1,3-dihydro-1λ$^5$-benzo[c][1,2] oxaphosphole (4u),
3-Nonyl-1,1,1-triphenyl-1,3-dihydro-1λ$^5$-benzo[c][1,2]oxaphosphole (4v),
1,1,1-Triphenyl-3-vinyl-1,3-dihydro-1λ$^5$-benzo[c][1,2]oxaphosphole (4w),
1,1,1-Triphenyl-3-styryl-1,3-dihydro-1λ$^5$-benzo[c][1,2]oxaphosphole (4x),
3-(4-Methoxystyryl)-1,1,1-triphenyl-1,3-dihydro-1λ$^5$-benzo[c][1,2]oxaphosphole (4y),
3-(4-Chlorophenyl)-5,6-dimethyl-1,1,1-triphenyl-1,3-dihydro-1λ$^5$ benzo[c][1,2]oxaphosphole (4z),
3-(4-Chlorophenyl)-5,6-difluoro-1,1,1-triphenyl-1,3-dihydro-1λ$^5$-benzo[c][1,2] oxaphosphole (4aa),
3-(4-Chlorophenyl)-1,1,1-triphenyl-1,3-dihydro-1λ$^5$[1,3]dioxolo [4',5':4,5]benzo [1,2-c][1,2]oxaphosphole (4ab),
3-(4-Chlorophenyl)-1,1,1-triphenyl-3,5,6,7-tetrahydro-1H-1λ$^5$-indeno[5,6-c][1,2]oxaphosphole (4ac),
1-(4-Chlorophenyl)-3,3,3-triphenyl-1,3-dihydro-3λ$^5$-naphtho[2,1-c][1,2]oxaphosphole (4ad),
3-(4-Chlorophenyl)-5-methyl-1,1,1-triphenyl-1,3-dihydro-1λ$^5$-benzo[c][1,2] oxaphosphole (4ae),
3-(4-Chlorophenyl)-6-methyl-1,1,1-triphenyl-1,3-dihydro-1λ$^5$-benzo[c][1,2] oxaphosphole (4ae'),
3-(4-Chlorophenyl)-5-fluoro-1,1,1-triphenyl-1,3-dihydro-1λ$^5$-benzo [c][1,2]oxaphosphole (4af),
3-(4-Chlorophenyl)-6-fluoro-1,1,1-triphenyl-1,3-dihydro-1λ$^5$-benzo[c][1,2]oxaphosphole (4af'),
3-(4-Chlorophenyl)-1,1,1-tri-p-tolyl-1,3-dihydro-1λ$^5$-benzo[c][1,2]oxaphosphole (4ag),
3-(4-Chlorophenyl)-1,1,1-tris(4-methoxyphenyl)-1,3-dihydro-1λ$^5$-benzo[c] [1,2]oxaphosphole (4ah),
3-(4-Chlorophenyl)-1,1,1-tri-o-tolyl-1,3-dihydro-1λ$^5$-benzo[c][1,2]oxaphosphole (4ai),
3-(4-Chlorophenyl)-1,1-diphenyl-1-(p-tolyl)-1,3-dihydro-1λ$^5$-benzo[c][1,2]oxaphosphole (4aj),
1,1,1-Tributyl-3-(4-chlorophenyl)-1,3-dihydro-1λ$^5$-benzo[c] [1,2]oxaphosphole (4ak)

In one embodiment of the present invention a process for the preparation of benzoxaphosphole compounds of formula (I) comprising the steps of:
cooling the reaction mixture of 18-crown-6, KF and phosphine precursor in THF at −10° C. to −0° C. followed by stirring for 5-10 minutes;
adding aryne precursor to the reaction mixture of step (a) followed continued stirring for additional 5-10 minutes at −10° C. to 0° C.;
adding aldehyde to the reaction mixture of step (b) and continued stirring from −10° C. to room temperature (25-35° C.) for 12 h-15 h to obtain the compounds of formula (I).

In another embodiment of the present invention the reaction is carried out under argon atmosphere.

Still in another embodiment of the present invention the aryne precursors are selected from trimethylsilyl triflates optionally substituted with one or two substituents each of which is independently selected from alkyl, halogen, alkoxy, haloalkyl, cyano, nitro, hydroxy, aryl, naphthyl, phenanthryl and may optionally form carbocyclic ring or heterocyclic ring containing one or more heteroatoms selected from the group consisting of: O, N.

Still in another embodiment of the present invention the aryne precursors are preferably selected from 2-(trimethylsilyl)phenyl trifluoromethanesulfonate, 4,5-dimethyl-2-(trimethylsilyl)phenyl trifluoromethanesulfonate, 4,5-difluoro-2-(trimethylsilyl) phenyl trifluoromethanesulfonate, 6-(trimethylsilyl)benzo[d][1,3]dioxol-5-yl trifluoromethanesulfonate, 6-(trimethylsilyl)-2,3-dihydro-1H-inden-5-yl trifluoro-methanesulfonate, 2-(trimethylsilyl)naphthalen-1-yl trifluoromethanesulfonate, 5-methyl-2-(trimethylsilyl)phenyl trifluoromethanesulfonate, 4-fluoro-2-(trimethylsilyl)phenyl trifluoromethanesulfonate.

Still in another embodiment of the present invention the aldehydes are selected from aromatic aldehydes, aliphatic aldehydes, heterocyclic aldehydes, α,β-unsaturated aldehydes.

Still in another embodiment of the present invention the aldehydes are preferably selected from benzaldehyde, 4-chlorobenzaldehyde, 4-methoxybenzaldehyde, 4-methylbenzaldehyde, 4-bromobenzaldehyde, 4-fluorobenzaldehyde, 4-(trifluoromethyl)benzaldehyde, methyl 4-formylbenzoate, 4-formylbenzonitrile, 3-methoxybenzaldehyde, 3-bromobenzaldehyde, 3-nitrobenzaldehyde, 2-methylbenzaldehyde, 2-fluorobenzaldehyde, 3,4-dichlorobenzaldehyde, 2,4, 6-trimethylbenzaldehyde, 2-naphthaldehyde, pyrene-4-carbaldehyde, benzofuran-2-carbaldehyde, thiophene-2-carbaldehyde, cyclohexanecarbaldehyde, decanal, acrylaldehyde, trans cinnamaldehyde, (E)-3-(4-methoxyphenyl)acrylaldehyde.

Still in another embodiment of the present invention phosphine precursors are preferably selected from tri-p-tolylphosphane, tris(4-methoxyphenyl)phosphane, tri-o-tolylphosphane, diphenyl (p-tolyl)phosphane, tri-n-butylphosphine.

Still in another embodiment of the present invention yield of benzoxaphosphole compounds of formula (I) is in the range of 55-95%.

Advantages of the Invention

Novel compounds
Transition-metal-free approach
One pot—one step process with good yields
Stable P—O bond created

DETAILED DESCRIPTION OF THE INVENTION

Accordingly, the main embodiment of the present invention provides a compound of formula (I),

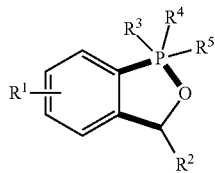

Formula (I)

wherein,

R¹ is selected from hydrogen, alkyl, halogen, OMe, —OCH₂O—, —(CH₂)₃—, —(CH₂)₄-naphthyl, phenanthryl;

R² is selected from various aromatic aldehydes (electron releasing, electron withdrawing and neutral), aliphatic aldehydes, heterocyclic aldehydes, α,β-unsaturated aldehydes; and R³, R⁴, R⁵ are independently selected from aryl, heteroaryl, alkyl phosphines.

In another embodiment of the present invention, wherein the compounds of formula (I) are preferably selected from group comprising, 3-(4-Chlorophenyl)-1,1,1-triphenyl-1,3-dihydro-1λ⁵-benzo[c][1,2]oxaphosphole (4a)

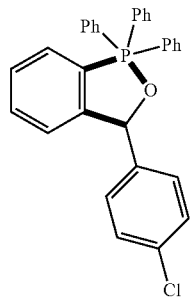

3-(4-Methoxyphenyl)-1,1,1-triphenyl-1,3-dihydro-1λ⁵-benzo[c][1,2]oxaphosphole (4b)

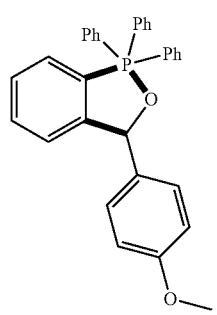

1,1,1-Triphenyl-3-(p-tolyl)-1,3-dihydro-1λ⁵-benzo[c][1,2]oxaphosphole (4c)

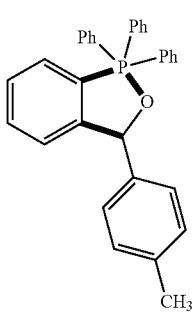

3-(4-Bromophenyl)-1,1,1-triphenyl-1,3-dihydro-1λ⁵-benzo[c][1,2]oxaphosphole (4d)

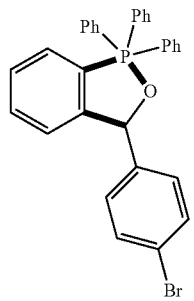

1,1,1,3-Tetraphenyl-1,3-dihydro-1λ⁵-benzo[c][1,2] oxaphosphole (4e)

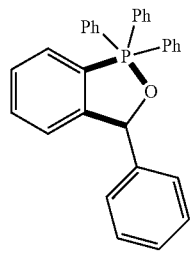

3-(4-Fluorophenyl)-1,1,1-triphenyl-1,3-dihydro-1λ⁵-benzo[c][1,2]oxaphosphole (4f)

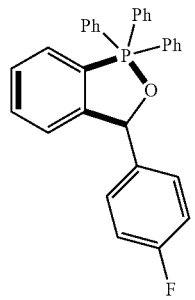

1,1,1-Triphenyl-3-(4-(trifluoromethyl)phenyl)-1,3-dihydro-1λ⁵-benzo[c][1,2] oxaphosphole (4g)

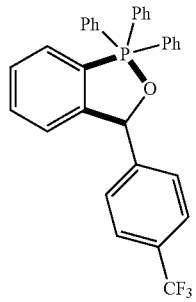

Methyl-4-(1,1,1-triphenyl-1,3-dihydro-1λ⁵-benzo[c][1,2] oxaphosphol-3-yl) benzoate (4h)

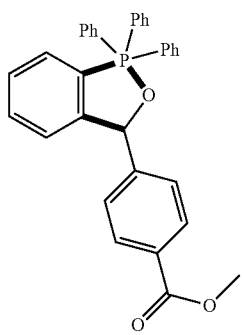

4-(1,1,1-Triphenyl-1,3-dihydro-1λ⁵-benzo[c][1,2] oxaphosphol-3-yl)benzonitrile (4i)

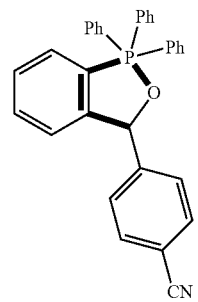

3-(3-Methoxyphenyl)-1,1,1-triphenyl-1,3-dihydro-1λ⁵-benzo [c][1,2]oxaphosphole (4j)

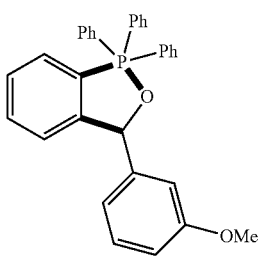

3-(3-Bromophenyl)-1,1,1-triphenyl-1,3-dihydro-1λ⁵-benzo[c][1,2]oxaphosphole (4k)

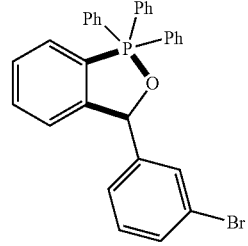

3-(3-Nitrophenyl)-1,1,1-triphenyl-1,3-dihydro-1λ⁵-benzo[c][1,2]oxaphosphole (4l)

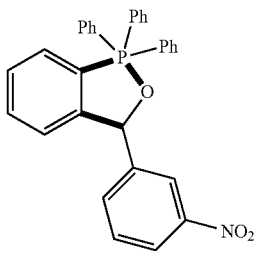

1,1,1-Triphenyl-3-(o-tolyl)-1,3-dihydro-1λ⁵-benzo[c][1,2] oxaphosphole (4m)

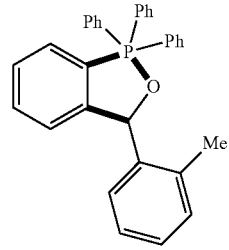

3-(2-Fluorophenyl)-1,1,1-triphenyl-1,3-dihydro-1λ⁵-benzo[c][1,2]oxaphosphole (4n)

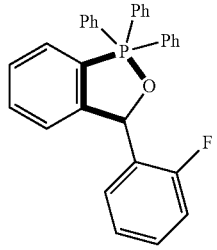

3-(3,4-Dichlorophenyl)-1,1,1-triphenyl-1,3-dihydro-1λ⁵-benzo[c][1,2]oxaphosphole (4o)

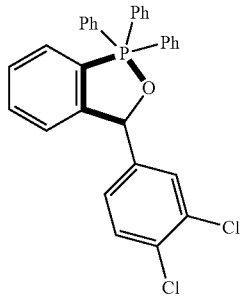

3-Mesityl-1,1,1-triphenyl-1,3-dihydro-1λ⁵-benzo[c][1,2]oxaphosphole (4p)

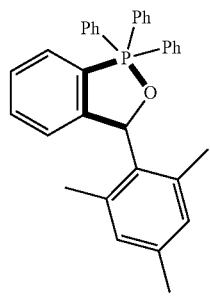

3-(Naphthalen-2-yl)-1,1,1-triphenyl-1,3-dihydro-1λ⁵-benzo[c][1,2]oxaphosphole (4q)

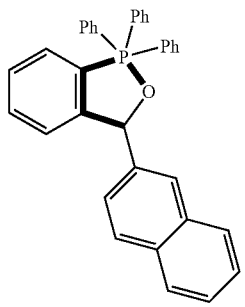

1,1,1-Triphenyl-3-(pyren-4-yl)-1,3-dihydro-1λ⁵-benzo[c][1,2]oxaphosphole (4r)

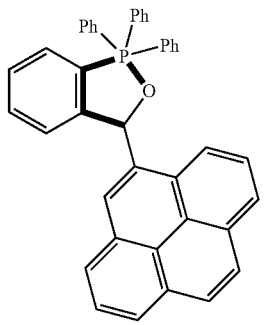

3-(Benzofuran-2-yl)-1,1,1-triphenyl-1,3-dihydro-1λ⁵-benzo[c][1,2]oxaphosphole (4s)

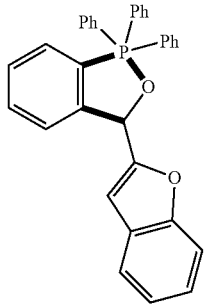

1,1,1-Triphenyl-3-(thiophen-2-yl)-1,3-dihydro-1λ⁵-benzo[c][1,2]oxaphosphole (4t)

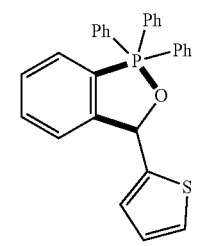

3-Cyclohexyl-1,1,1-triphenyl-1,3-dihydro-1λ⁵-benzo[c][1,2]oxaphosphole (4u)

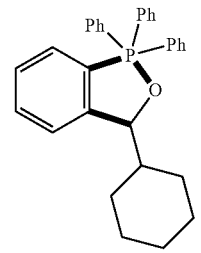

3-Nonyl-1,1,1-triphenyl-1,3-dihydro-1λ⁵-benzo[c][1,2]oxaphosphole (4v)

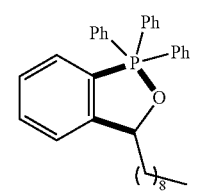

1,1,1-Triphenyl-3-vinyl-1,3-dihydro-1λ⁵-benzo[c][1,2]oxaphosphole (4w)

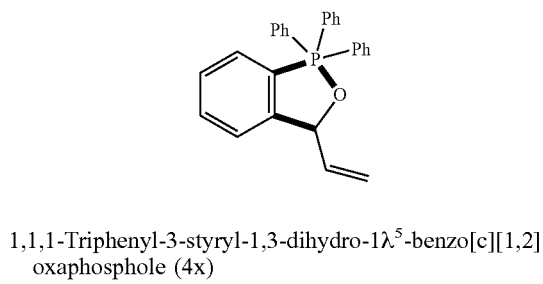

1,1,1-Triphenyl-3-styryl-1,3-dihydro-1λ⁵-benzo[c][1,2]
oxaphosphole (4x)

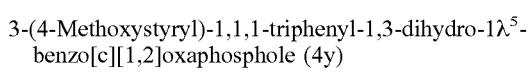

3-(4-Methoxystyryl)-1,1,1-triphenyl-1,3-dihydro-1λ⁵-
benzo[c][1,2]oxaphosphole (4y)

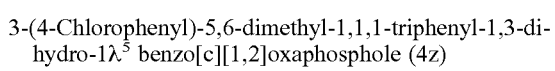

3-(4-Chlorophenyl)-5,6-dimethyl-1,1,1-triphenyl-1,3-di-
hydro-1λ⁵ benzo[c][1,2]oxaphosphole (4z)

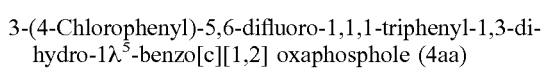

3-(4-Chlorophenyl)-5,6-difluoro-1,1,1-triphenyl-1,3-di-
hydro-1λ⁵-benzo[c][1,2] oxaphosphole (4aa)

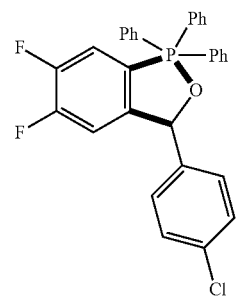

3-(4-Chlorophenyl)-1,1,1-triphenyl-1,3-dihydro-1λ⁵[1,3]di-
oxolo [4',5':4,5]benzo [1,2-c][1,2]oxaphosphole (4ab)

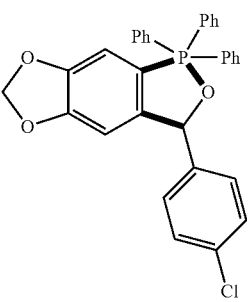

3-(4-Chlorophenyl)-1,1,1-triphenyl-3,5,6,7-tetrahydro-1H-
1λ⁵-indeno[5,6-c][1,2]oxaphosphole (4ac)

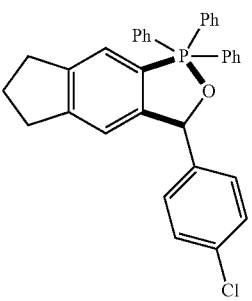

1-(4-Chlorophenyl)-3,3,3-triphenyl-1,3-dihydro-3λ⁵-naph-
tho[2,1-c][1,2]oxaphosphole (4ad)

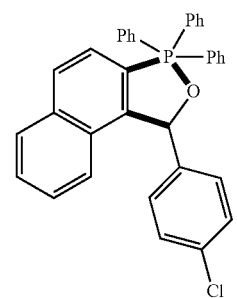

3-(4-Chlorophenyl)-5-methyl-1,1,1-triphenyl-1,3-dihydro-1λ⁵-benzo[c][1,2] oxaphosphole (4ae)

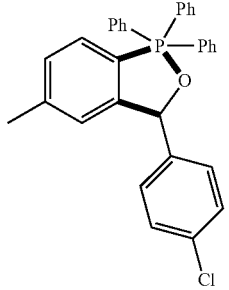

4ae 3-(4-Chlorophenyl)-6-methyl-1,1,1-triphenyl-1,3-dihydro-1λ⁵-benzo[c][1,2] oxaphosphole (4ae')

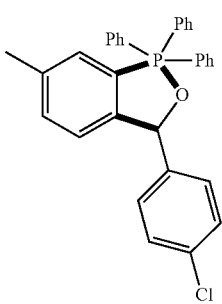

4ae'

3-(4-Chlorophenyl)-5-fluoro-1,1,1-triphenyl-1,3-dihydro-1λ⁵-benzo [c][1,2]oxaphosphole (4af)

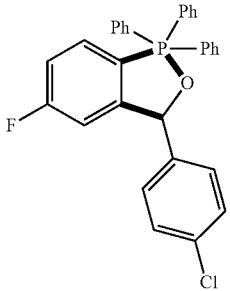

4af 3-(4-Chlorophenyl)-6-fluoro-1,1,1-triphenyl-1,3-dihydro-1λ⁵-benzo[c][1,2]oxaphosphole (4af')

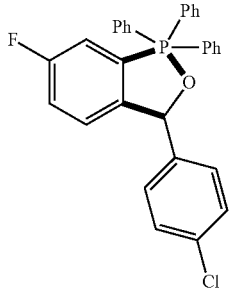

4af'

3-(4-Chlorophenyl)-1,1,1-tri-p-tolyl-1,3-dihydro-1λ⁵-benzo[c][1,2]oxaphosphole (4ag)

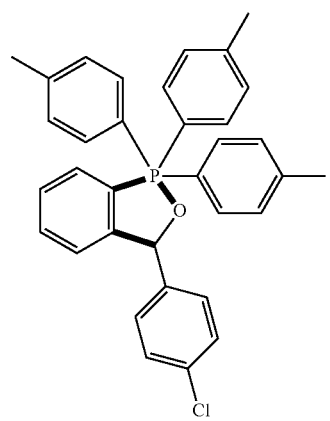

4ag 3-(4-Chlorophenyl)-1,1,1-tris(4-methoxyphenyl)-1,3-dihydro-1λ⁵-benzo[c] [1,2]oxaphosphole (4ah)

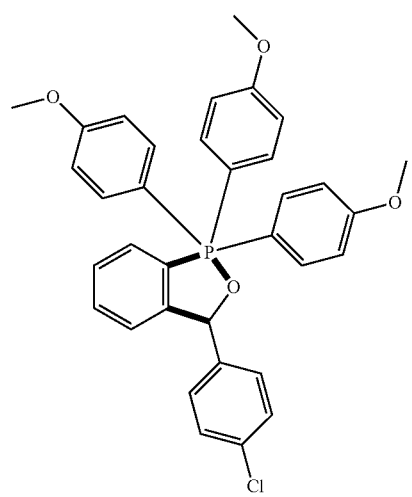

4ah 3-(4-Chlorophenyl)-1,1,1-tri-o-tolyl-1,3-dihydro-1λ⁵-benzo[c][1,2]oxaphosphole (4ai)

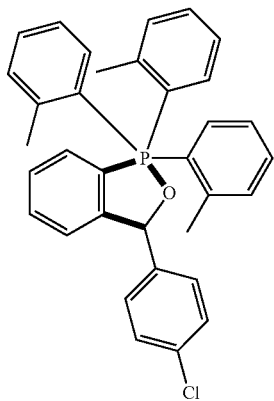

3-(4-Chlorophenyl)-1,1-diphenyl-1-(p-tolyl)-1,3-dihydro-1λ⁵-benzo[c][1,2]oxaphosphole (4aj)

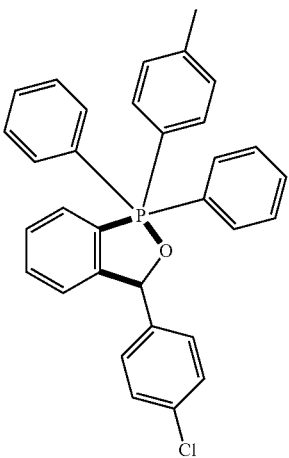

1,1,1-Tributyl-3-(4-chlorophenyl)-1,3-dihydro-1λ⁵-benzo[c][1,2]oxaphosphole (4ak)

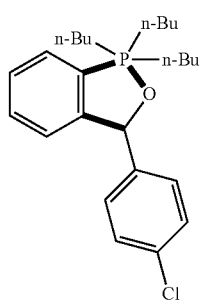

Another embodiment of the present invention provides a process for the preparation of benzoxaphosphole compounds of formula (I), wherein the process comprising the steps of:

cooling the reaction mixture of 18-crown-6, KF and phosphine precursor in THF at −10° C. to −0° C. followed by stirring for 5-10 minutes;

adding aryne precursor to the reaction mixture of step (a) followed continued stirring for additional 5-10 minutes at −10° C. to 0° C.;

adding aldehyde to the reaction mixture of step (b) and continued stirring from −10° C. to room temperature (25-35° C.) for 12 h-15 h to obtain the compounds of formula (I).

a. In another embodiment of the present invention, wherein the reaction is carried out under argon atmosphere.

b. In another embodiment of the present invention, wherein the aryne precursors are selected from trimethylsilyl triflates optionally substituted with one or two substituents each of which is independently selected from alkyl, halogen, alkoxy, haloalkyl, cyano, nitro, hydroxy, aryl, naphthyl, phenanthryl and may optionally form carbocyclic ring or heterocyclic ring containing one or more heteroatoms selected from the group consisting of: O, N.

c. In another embodiment of the present invention, wherein the aryne precursors are preferably selected from 2-(trimethylsilyl)phenyl trifluoromethanesulfonate, 4,5-dimethyl-2-(trimethylsilyl)phenyl trifluoromethanesulfonate, 4,5-difluoro-2-(trimethylsilyl) phenyl trifluoromethanesulfonate, 6-(trimethylsilyl)benzo[d][1,3]dioxol-5-yl trifluoromethanesulfonate, 6-(trimethylsilyl)-2,3-dihydro-1H-inden-5-yl trifluoro-methanesulfonate, 2-(trimethylsilyl)naphthalen-1-yl trifluoromethanesulfonate, 5-methyl-2-(trimethylsilyl) phenyl trifluoromethanesulfonate, 4-fluoro-2-(trimethylsilyl)phenyl trifluoromethanesulfonate.

d. In another embodiment of the present invention, wherein the aldehydes are selected from aromatic aldehydes, aliphatic aldehydes, heterocyclic aldehydes, α,β-unsaturated aldehydes.

e. In another embodiment of the present invention, wherein the aldehydes are preferably selected from benzaldehyde, 4-chlorobenzaldehyde, 4-methoxybenzaldehyde, 4-methylbenzaldehyde, 4-bromobenzaldehyde, 4-fluorobenzaldehyde, 4-(trifluoromethyl)benzaldehyde, methyl 4-formylbenzoate, 4-formylbenzonitrile, 3-methoxybenzaldehyde, 3-bromobenzaldehyde, 3-nitrobenzaldehyde, 2-methylbenzaldehyde, 2-fluorobenzaldehyde, 3,4-dichlorobenzaldehyde, 2,4, 6-trimethylbenzaldehyde, 2-naphthaldehyde, pyrene-4-carbaldehyde, benzofuran-2-carbaldehyde, thiophene-2-carbaldehyde, cyclohexanecarbaldehyde, decanal, acrylaldehyde, trans cinnamaldehyde, (E)-3-(4-methoxyphenyl) acrylaldehyde.

f. In another embodiment of the present invention, wherein phosphine precursors are preferably selected from tri-p-tolylphosphane, tris(4-methoxyphenyl)phosphane, tri-o-tolylphosphane, diphenyl (p-tolyl)phosphane, tri-n-butyl-phosphine.

g. In another embodiment of the present invention, wherein yield of benzoxaphosphole compounds of formula (I) is in the range of 55-95%.

Further, the present invention provides a process for the preparation of novel benzoxaphosphole compounds of formula (I) comprising the step of:

cooling the predation mixture of 18-crown-6, KF and phosphine precursor in THF at −10° C. followed by stirring for 5 minutes;

adding aryne precursor to the reaction mixture of step (a) followed continued stirring for additional 5 minutes at −10° C.;

adding aldehyde to the reaction mixture of step (b) and continued stirring from 10° C. to room temperature for 12 h to afford the compounds of formula (I);

a. Wherein, the reaction is carried out under argon atmosphere.

The process for preparation of novel benzoxaphosphole compounds of Formula (I) is as shown below in Scheme 1:

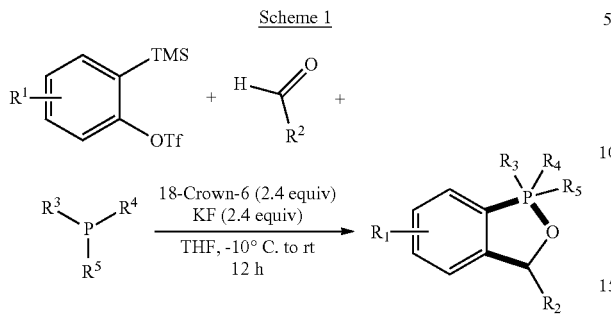

Scheme 1

The aryne precursor are selected from trimethylsilyl triplanes optionally substituted with one or two substituents each of which is independently selected from alkyl, halogen, alkoxy, haloalkyl, cyano, nitro, hydroxy, aryl, naphthyl, phenanthryl and may optionally form carbocyclic ring or heterocyclic ring containing one or more heteroatoms selected from the group consisting of: O, N.

The aryne precursors used for the preparation of novel benzoxaphosphole compounds of formula (I) are preferably selected from 2-(trimethylsilyl)phenyl trifluoromethanesulfonate, 4,5-dimethyl-2-(trimethylsilyl)phenyl trifluoromethanesulfonate, 4,5-difluoro-2-(trimethylsilyl) phenyl trifluoromethane-sulfonate, 6-(trimethylsilyl)benzo[d] [1,3] dioxol-5-yl trifluoromethanesulfonate, 6-(trimethylsilyl)-2,3-dihydro-1H-inden-5-yl trifluoro-methanesulfonate, 2-(trimethylsilyl) naphthalen-1-yl trifluoromethanesulfonate, 5-methyl-2-(trimethylsilyl)phenyl trifluoro-methanesulfonate, 4-fluoro-2-(trimethylsilyl)phenyl trifluoromethanesulfonate.

The aldehyde are selected from aromatic aldehydes, aliphatic aldehydes, heterocyclic aldehydes, α,β-unsaturated aldehydes.

The aldehydes used for the preparation of novel benzoxaphosphole compounds of formula (I) are preferably selected from benzaldehyde, 4-chlorobenzaldehyde, 4-methoxybenzaldehyde, 4-methylbenzaldehyde, 4-bromobenzaldehyde, 4-fluorobenzaldehyde, 4-(trifluoromethyl) benzaldehyde, methyl 4-formylbenzoate, 4-formylbenzonitrile, 3-methoxybenzaldehyde, 3-bromobenzaldehyde, 3-nitrobenzaldehyde, decanal, 2-methylbenzaldehyde, 2-fluorobenzaldehyde, 3,4-dichlorobenzaldehyde, 2,4,6-trimethylbenzaldehyde, 2-naphthaldehyde, pyrene-4-carbaldehyde, benzofuran-2-carbaldehyde, acrylaldehyde, thiophene-2-carbaldehyde, cyclohexanecarbaldehyde, trans cinnamaldehyde, (E)-3-(4-methoxyphenyl) acrylaldehyde.

The phosphine precursors used for the preparation of novel benzoxaphosphole compounds of formula (I) are preferably selected from tri-p-tolylphosphane, tris(4-methoxyphenyl)phosphane, tri-o-tolylphosphane, diphenyl (p-tolyl)phosphane, tri-n-butylphosphine.

In an aspect, the present invention provides a process for the preparation of novel benzoxaphosphole compounds of formula (I) wherein the reaction proceeds via the initial generation of a 1,3-zwitterionic intermediate from phosphine and aryne, which undergoes a formal [3+2] cycloaddition with aldehydes allowing the synthesis of phosphorus heterocycles The present invention provides a process for the preparation of novel benzoxaphosphole compounds of formula (I) wherein the ratio of each reactant is shown below:

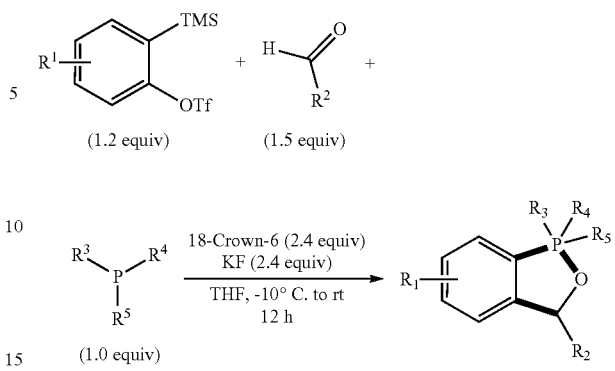

EXAMPLES

The following examples are given by way of illustration only and therefore should not be construed to limit the scope of the present invention.

General procedure for preparation of compound of formula (I):

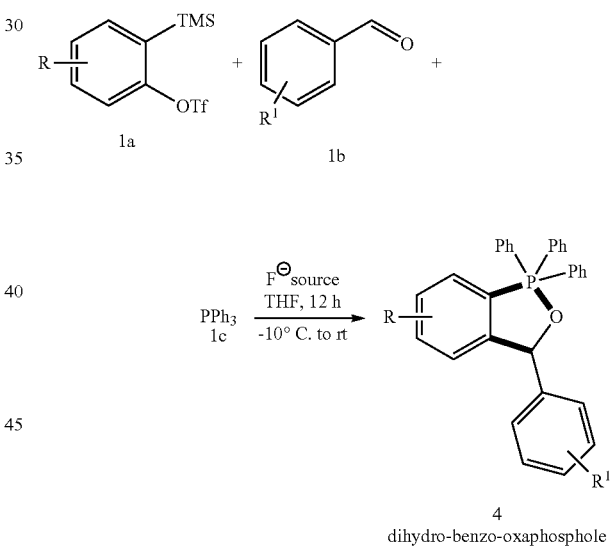

4
dihydro-benzo-oxaphosphole

To a flame-dried screw-capped Schlenk tube equipped with a magnetic stir bar was added 18-crown-6 (0.634 g, 2.40 mmol), KF (Potassium fluoride) (0.140 g, 2.40 mmol) and triphenyl phosphine 1c (1.0 mmol). Then the screw-capped tube was evacuated and backfilled with argon. The mixture was dissolved in THF (6.0 mL) under argon atmosphere and cooled to −10° C. and continued stirring for 5 minutes. To the stirring solution was added the aryne precursor 1a and continued stirring for additional 5 minutes at −10° C. Finally added the aldehyde 1b to the reaction mixture and continued stirring from −10° C. to room temperature for 12 h. Then the crude reaction mixture was purified by column chromatography on silica gel to afford the corresponding product.

Example 1: Synthesis of 3-(4-Chlorophenyl)-1,1,1-triphenyl-1,3-dihydro-1λ⁵-benzo [c][1,2]oxaphosphole (4a)

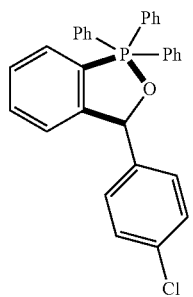

Following the general procedure, treatment of 2-(trimethylsilyl)phenyl trifluoromethanesulfonate 1a (0.358 g, 292 µL, 1.20 mmol) and 4-chlorobenzaldehyde 1b (0.211 g, 1.50 mmol) with triphenylphosphine 1c (0.262 g, 1.0 mmol) in the presence of KF (0.140 g, 2.40 mmol) and 18-crown-6 (0.634 g, 2.40 mmol) in THF (6.0 mL) at (−)10° C. to rt for 12 h followed by flash column chromatography (Pet. ether/EtOAc=40/60) of the crude reaction mixture using silica gel afforded 3-(4-chlorophenyl)-1,1,1-triphenyl-1,3-dihydro-1λ⁵-benzo[c][1,2]oxaphosphole 4a as a white solid (0.389 g, 81% yield).

$R_f$ (EtOAc): 0.41; $^1$H NMR (500 MHz, CDCl$_3$) δ 7.47 (t, J=6.6 Hz, 1H, H$_{ar}$), 7.41-7.37 (m, 6H, H$_{ar}$), 7.35-7.31 (m, 9H, H$_{ar}$), 7.23-7.20 (m, 4H, H$_{ar}$), 7.08 (d, J=7.9 Hz, 2H, H$_{ar}$), 6.87 (t, J=10.7 Hz, 1H, H$_{ar}$), 5.60 (s, 1H, CH). $^{13}$C NMR (125 MHz, CDCl$_3$) δ 153.92 (d, J=21.5 Hz), 143.72, 142.93, 136.56 (d, J=21.5 Hz), 132.95, 132.31 (d, J=2.4 Hz), 131.42 (d, J=8.8 Hz), 129.16, 129.02, 128.38, 128.13, 127.96, 127.53, 127.43, 127.36, 124.77 (d, J=15.4 Hz), 76.25. $^{31}$P NMR (203 MHz, CDCl$_3$) δ −51.41 HRMS (ESI) calculated [M+H]$^+$ for C$_{31}$H$_{25}$ClOP: 479.1326. found: 479.1327. FTIR (cm$^{-1}$) 3829, 3743, 3618, 3058, 3005, 1897, 1588, 1485, 1437, 1406, 1257, 1229, 1183, 1112, 1078, 1020, 886, 847, 745, 695, 663.

Example 2: Synthesis of 3-(4-Methoxyphenyl)-1,1,1-triphenyl-1,3-dihydro-1λ⁵-benzo[c][1,2] oxaphosphole (4b)

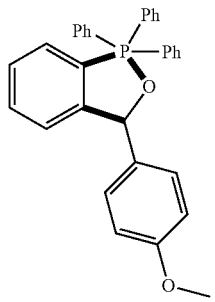

Following the general procedure, treatment of 2-(trimethylsilyl)phenyl trifluoromethanesulfonate 1a (0.179 g, 146 µL, 0.60 mmol) and 4-methoxybenzaldehyde 1b (0.102 g, 91 µL, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(4-methoxyphenyl)-1,1,1-triphenyl-1,3-dihydro-1λ⁵-benzo[c][1,2]oxaphosphole 4b as a white solid (0.182 g, 77% yield).

$R_f$ (EtOAc): 0.38; $^1$H NMR (400 MHz, CDCl$_3$) δ 7.49-7.46 (m, 1H, H$_{ar}$), 7.42-7.39 (m, 6H, H$_{ar}$), 7.33-7.29 (m, 9H, H$_{ar}$), 7.23 (t, J=5.8 Hz, 2H, H$_{ar}$), 7.11 (d, J=8.4 Hz, 2H, H$_{ar}$), 6.86-6.81 (m, 3H, H$_{ar}$), 5.52 (s, 1H, CH), 3.79 (s, 3H, CH$_3$). $^{13}$C NMR (100 MHz, CDCl$_3$) δ 158.98, 154.88 (d, J=21.6 Hz), 144.17, 143.11, 136.46 (d, J=6.5 Hz), 136.28, 132.15 (d, J=3.1 Hz), 131.59 (d, J=8.9 Hz), 129.12, 128.03, 127.41 (d, J=12.3 Hz), 127.26, 127.12, 124.90 (d, J=15.4 Hz), 113.69, 76.23, 55.32. $^{31}$P NMR (162 MHz, CDCl$_3$) δ −52.65. HRMS (ESI) calculated [M+H]$^+$ for C$_{32}$H$_{28}$O$_2$P: 475.1821. found: 475.1822. FTIR (cm$^{-1}$) 3843, 3649, 3005, 2361, 1836, 1741, 1693, 1647, 1484, 1436, 1246, 1216, 1118, 1050, 742, 699, 665.

Example 3: Synthesis of 1,1,1-Triphenyl-3-(p-tolyl)-1,3-dihydro-1λ⁵-benzo[c][1,2] oxaphosphole (4c)

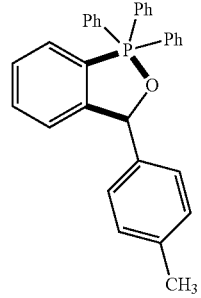

Following the general procedure, treatment of 2-(trimethylsilyl)phenyl trifluoromethanesulfonate 1a (0.179 g, 146 µL, 0.6 mmol) and 4-methylbenzaldehyde 1b (0.090 g, 88 µL, 0.75 mmol) with triphenylphosphine 1c (0.131 g, 0.5 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 1,1,1-triphenyl-3-(p-tolyl)-1,3-dihydro-1λ⁵-benzo[c][1,2]oxaphosphole 4c as a white solid (0.154 g, 67% yield).

$R_f$ (EtOAc): 0.44; $^1$H NMR (500 MHz, CDCl$_3$) δ 7.44 (t, J=6.2 Hz, 1H, H$_{ar}$), 7.39-7.35 (m, 6H, H$_{ar}$), 7.32-7.27 (m, 9H, H$_{ar}$), 7.22 (dd, =6.6 Hz, J$_2$=13.0 Hz, 2H, H$_{ar}$), 7.0-7.03 (m, 4H, H$_{ar}$), 6.82 (dd, J$_1$=8.3 Hz, J$_2$=10.3 Hz, 1H, H$_{ar}$), 5.51 (s, 1H, CH), 2.30 (s, 3H, CH$_3$). $^{13}$C NMR (125 MHz, CDCl$_3$) δ 154.75 (d, J=21.8 Hz), 144.06, 143.22, 141.23, 136.83, 136.37 (d, J=14.6 Hz), 132.17 (d, J=2.5 Hz), 131.58 (d, J=9.1 Hz), 128.96, 128.29, 128.0 (d, J=1.8 Hz), 127.26, 127.41 (d, J=12.5 Hz), 127.17 (d, J=14.1 Hz), 124.88 (d, J=15.6 Hz), 76.58. $^{31}$P NMR (203 MHz, CDCl$_3$) δ −52.08. HRMS (ESI) calculated [M+H]$^+$ for C$_{32}$H$_{28}$OP: 459.1872. found 459.1872. FTIR (cm$^{-1}$) 3843, 3013, 2361, 1835, 1647, 1515, 1214, 1033, 742, 666.

Example 4: Synthesis of 3-(4-Bromophenyl)-1,1,1-triphenyl-1,3-dihydro-1λ⁵-benzo [c] [1,2] oxaphosphole (4d)

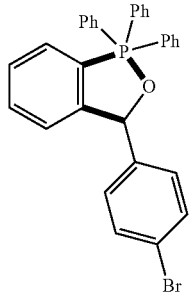

4d

Following the general procedure, treatment of 2-(trimethylsilyl)phenyl trifluoromethanesulfonate 1a (0.179 g, 146 μL, 0.60 mmol) and 4-bromobenzaldehyde 1b (0.137 g, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(4-bromophenyl)-1,1,1-triphenyl-1,3-dihydro-1λ⁵-benzo[c][1,2]oxaphosphole 4d as a white solid (0.223 g, 85% yield).

$R_f$ (EtOAc): 0.42; ¹H NMR (400 MHz, CDCl₃) δ 7.46 (t, J=6.4 Hz, 1H, $H_{ar}$), 7.37-7.35 (m, 5H, $H_{ar}$), 7.33-7.26 (m, 12H, $H_{ar}$), 7.23-7.17 (m, 2H, $H_{ar}$), 6.98 (d, J=8.3 Hz, 2H, $H_{ar}$), 6.84 (dd, $J_1$=8.2 Hz, $J_2$=11.2 Hz, 1H, $H_{ar}$), 5.56 (s, 1H, CH). ¹³C NMR (100 MHz, CDCl₃) δ 153.82 (d, J=21.2 Hz), 143.47, 142.38, 136.63 (d, J=14.5 Hz), 132.41 (d, J=2.7 Hz), 131.52 (d, J=8.8 Hz), 131.35, 129.55, 128.29, 127.56 (d, J=12.3 Hz), 127.40, 124.96 (d, J=14.9 Hz), 121.17, 76.30. ³¹P NMR (162 MHz, CDCl₃) δ −51.38 HRMS (ESI) calculated [M+H]⁺ for $C_{31}H_{25}BrOP$: 523.0821. found: 523.0825. FTIR (cm⁻¹) 3894, 3843, 3743, 3619, 2982. 2360, 1835, 1707, 1615, 1467, 1435, 1249, 1180, 1046, 844, 743, 665.

Example 5: Synthesis of 1,1,1,3-Tetraphenyl-1,3-dihydro-1λ⁵-benzo[c] [1,2] oxaphosphole (4e)

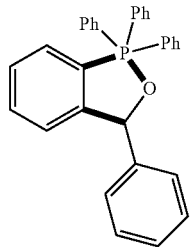

4e

Following the general procedure, treatment of 2-(trimethylsilyl)phenyl trifluoromethanesulfonate 1a (0.179 g, 146 μL, 0.60 mmol) and benzaldehyde 1b (0.105 g, 0.75 mmol) with triphenylphosphine 1c (0.080 g, 76 μL, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 1,1,1,3-tetraphenyl-1,3-dihydro-1λ⁵-benzo[c][1,2] oxaphosphole 4e as a white solid (0.180 g, 81% yield).

$R_f$ (EtOAc): 0.40; ¹H NMR (400 MHz, CDCl₃) δ 7.45-7.36 (m, 7H, $H_{ar}$), 7.31 (bs, 9H, $H_{ar}$), 7.26-7.22 (m, 5H, $H_{ar}$), 7.15 (d, J=7.1 Hz, 2H, $H_{ar}$), 6.83 (t, J=8.4 Hz, 1H, $H_{ar}$), 5.56 (s, 1H, CH). ¹³C NMR (100 MHz, CDCl₃) δ 154.44 (d, J=21.4 Hz), 144.17, 143.62 (d, J=12.5 Hz), 142.65, 142.55, 136.46 (d, J=14.5 Hz), 132.27 (d, J=2.3 Hz), 131.64 (d, J=8.8 Hz), 128.28, 128.21, 127.92, 127.57, 127.44, 127.34, 127.21, 125.01 (d, J=15.5 Hz), 76.74. ³¹P NMR (162 MHz, CDCl₃) δ −48.23 HRMS (ESI) calculated [M+H]⁺ for $C_{31}H_{26}ClOP$: 445.1716. found: 445.1718. FTIR (cm⁻¹) 3860, 3677, 3619, 3013, 2362, 1741, 1693, 1647, 1516, 1462, 1216, 1117, 1057, 741, 667, 633.

Example 6: Synthesis of 3-(4-Fluorophenyl)-1,1,1-triphenyl-1,3-dihydro-1λ⁵-benzo [c][1,2]oxaphosphole (4f)

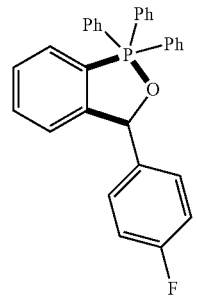

4f

Following the general procedure, treatment of 2-(trimethylsilyl)phenyl trifluoromethanesulfonate 1a (0.179 g, 146 μL, 0.6 mmol) and 4-fluorobenzaldehyde 1b (0.093 g, 81 μL, 0.75 mmol) with triphenylphosphine 1c (0.131 g, 0.5 mmol) in the presence of KF (0.070 g, 1.2 mmol) and 18-crown-6 (0.317 g, 1.2 mmol) in THF (3.0 mL) at −10° C. to rt for 12 h followed by flash column chromatography (Pet. ether/EtOAc=40/60) of the crude reaction mixture using silica gel afforded 3-(4-fluorophenyl)-1,1,1-triphenyl-1,3-dihydro-1λ⁵-benzo[c][1,2]oxaphosphole 4f as a white solid (0.181 g, 78% yield).

$R_f$ (EtOAc): 0.53; ¹H NMR (500 MHz, CDCl₃) δ 7.49 (t, J=6.5 Hz, 1H, $H_{ar}$), 7.40-7.36 (m, 6H, $H_{ar}$), 7.33-7.29 (m, 9H, $H_{ar}$), 7.27 (dd, =7.2 Hz, $J_2$=12.9 Hz, 1H, $H_{ar}$), 7.20 (d, J=7.2 Hz, 1H, $H_{ar}$), 7.14 (dd, =5.7 Hz, $J_2$=8.5 Hz, 2H, $H_{ar}$), 6.94 (t, J=8.8 Hz, 2H, $H_{ar}$), 6.88 (dd, =8.1 Hz, $J_2$=11.0 Hz, 1H, $H_{ar}$), 5.57 (s, 1H, CH). ¹³C NMR (125 MHz, CDCl₃) δ 162.25 (d, J=244.6 Hz), 154.33 (d, J=21.6 Hz), 140.13, 136.54 (d, J=14.5 Hz), 132.28 (d, J=2.6 Hz), 131.49 (d, J=8.9 Hz), 29.46 (d, J=8.2 Hz), 128.14, 127.54, 127.44, 127.32, 124.83 (d, J=15.0 Hz), 115.17, 115.0, 76.19. ³¹P NMR (203 MHz, CDCl₃) δ −51.96 HRMS (ESI) calculated [M+H]⁺ for $C_{31}H_{25}FOP$: 463.1622. found: 463.1649. FTIR (cm⁻¹) 3677, 3060, 2805, 1646, 1507, 1437, 1260, 1103, 827, 742.

Example 7: Synthesis of 1,1,1-Triphenyl-3-(4-(trifluoromethyl)phenyl)-1,3-dihydro-1λ⁵-benzo[c][1,2]oxaphosphole (4g)

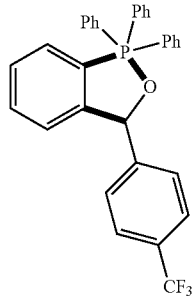

4g

Following the general procedure, treatment of 2-(trimethylsilyl)phenyl trifluoromethanesulfonate 1a (0.179 g, 146 µL, 0.6 mmol) and 4-(trifluoromethyl)benzaldehyde 1b (0.131 g, 102 µL, 0.75 mmol) with triphenylphosphine 1c (0.131 g, 0.5 mmol) in the presence of KF (0.070 g, 1.2 mmol) and 18-crown-6 (0.317 g, 1.2 mmol) in THF (3.0 mL) at −10° C. to rt for 12 h followed by flash column chromatography (Pet. ether/EtOAc=40/60) of the crude reaction mixture using silica gel afforded 1,1,1-Triphenyl-3-(4-(trifluoromethyl)phenyl)-1,3-dihydro-1λ⁵-benzo[c][1,2]oxaphosphole 4g as a white solid (0.199 g, 78% yield).

$R_f$ (EtOAc): 0.58; ¹H NMR (500 MHz, CDCl₃) δ 7.47 (d, J=8.0 Hz, 3H, $H_{ar}$), 7.38-7.28 (m, 15H, $H_{ar}$), 7.24-7.19 (m, 4H, $H_{ar}$), 6.89 (dd, =8.3 Hz, J₂=11.2 Hz, 1H, $H_{ar}$), 5.68 (s, 1H, CH). ¹³C NMR (125 MHz, CDCl₃) δ 153.37 (d, J=21.2 Hz), 148.43, 143.40, 142.55, 136.69 (d, J=14.3 Hz), 132.38 (d, J=2.9 Hz), 132.13 (d, J=9.8 Hz), 132.00 (d, J=2.4 Hz), 131.34 (d, J=8.8 Hz), 129.35 (q, J=31.83 Hz), 128.20, 127.91, 127.49 (d, J=13.4 Hz), 125.15 (d, J=3.5 Hz), 124.74 (d, J=15.2 Hz), 76.46. ³¹P NMR (203 MHz, CDCl₃) δ −50.16. HRMS (ESI) calculated [M+H]⁺ for C₃₂H₂₅F₃OP: 513.1590. found: 513.1602. FTIR (cm⁻¹) 3842, 3062, 2360, 1916, 1583, 1486, 1198, 1027, 739, 664.

Example 8: Synthesis of Methyl-4-(1,1,1-triphenyl-1,3-dihydro-1λ⁵-benzo[c][1,2] oxaphosphol-3-yl)benzoate (4h)

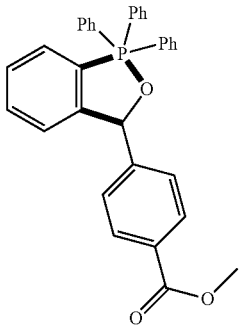

4h

Following the general procedure, treatment of 2-(trimethylsilyl)phenyl trifluoromethanesulfonate 1a (0.179 g, 146 µL, 0.60 mmol) and methyl 4-formylbenzoate 1b (0.123 g, 0.75 mmol) with triphenylphosphine 1c (0.131 g, 0.50 mmol) in the presence of KF (0.070 g, 1.20 mmol) and 18-crown-6 (0.317 g, 120 mmol) in THF (3.0 mL) at −10° C. to rt for 12 h followed by flash column chromatography (Pet. ether/EtOAc=40/60) of the crude reaction mixture using silica gel afforded methyl-4-(1,1,1-triphenyl-1,3-dihydro-1λ⁵-benzo[c][1,2]oxaphosphol-3-yl)benzoate 4h as a white solid (0.227 g, 90% yield).

$R_f$ (EtOAc): 0.47; ¹H NMR (500 MHz, CDCl₃) δ 7.93 (d, J=6.9 Hz, 2H, $H_{ar}$), 7.48 (t, J=6.5 Hz, 1H, $H_{ar}$), 7.40-7.37 (m, 6H, $H_{ar}$), 7.33-7.29 (m, 9H, $H_{ar}$), 7.27-7.24 (m, 1H, $H_{ar}$), 7.21 (d, J=7.2 Hz, 3H, $H_{ar}$), 6.87 (t, J=9.2 Hz, 1H, $H_{ar}$), 5.70 (s, 1H, CH), 3.90 (s, 3H, CH₃). ¹³C NMR (125 MHz, CDCl₃) δ 167.19, 153.56 (d, J=21.5 Hz), 149.72, 143.72, 142.88, 136.71 (d, J=14.6 Hz), 132.39 (d, J=2.5 Hz), 131.43 (d, J=8.7 Hz), 129.68, 129.06, 128.83, 128.19, 127.70, 127.58, 127.48, 124.75 (d, J=15.2 Hz), 76.70, 52.09. ³¹P NMR (203 MHz, CDCl₃) δ −50.75 HRMS (ESI) calculated [M+H]⁺ for C₃₃H₂₈O₃P: 503.1771. found: 503.1788. FTIR (cm⁻¹) 3829, 3744, 3678, 3649, 3008, 2319, 1712, 1647, 1614. 1469. 1369. 1279, 1217, 1112, 1041, 986, 872, 834.

Example 9: Synthesis of 4-(1,1,1-Triphenyl-1,3-dihydro-1λ⁵-benzo[c][1,2]oxaphosphol-3-yl)benzonitrile (4i)

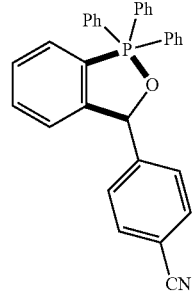

4i

Following the general procedure, treatment of 2-(trimethylsilyl)phenyl trifluoromethanesulfonate 1a (0.179 g, 146 µL, 0.60 mmol) and 4-formylbenzonitrile 1b (0.098 g, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 4-(1,1,1-triphenyl-1,3-dihydro-1λ⁵-benzo[c][1,2]oxaphosphol-3-yl)benzonitrile 4i as a white solid (0.206 g, 83% yield).

$R_f$ (EtOAc): 0.51; ¹H NMR (400 MHz, CDCl₃) δ 7.51 (d, J=6.7 Hz, 3H, $H_{ar}$), 7.37-7.28 (m, 16H, $H_{ar}$), 7.20 (d, J=7.2 Hz, 3H, $H_{ar}$), 6.90 (t, J=8.5 Hz, 1H, $H_{ar}$), 5.73 (s, 1H, CH). ¹³C NMR (100 MHz, CDCl₃) δ 152.84 (d, J=21.4 Hz), 150.03, 143.56, 142.54, 136.93 (d, J=14.6 Hz), 132.59, 132.15, 131.38 (d, J=8.4 Hz), 128.39, 128.29, 127.80, 127.64 (d, J=12.3 Hz), 124.75, 119.11, 110.95, 76.57. ³¹P NMR (162 MHz, CDCl₃) δ −50.08. HRMS (ESI) calculated [M+H]⁺ for C₃₂H₂₅NOP: 470.1668. found: 470.1672. FTIR (cm⁻¹) 3829, 3677, 3005, 1735, 1645, 1595, 1487, 1399, 1373, 1249, 1111, 1062, 846, 744, 699.

Example 10: Synthesis of 3-(3-Methoxyphenyl)-1,1,1-triphenyl-1,3-dihydro-1λ⁵-benzo [c][1,2] oxaphosphole (4j)

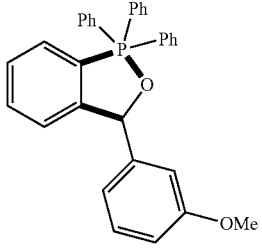

4j

Following the general procedure, treatment of 2-(trimethylsilyl)phenyl trifluoromethanesulfonate 1a (0.179 g, 146 μL, 0.6 mmol) and 3-methoxybenzaldehyde 1b (0.102 g, 91 μL, 0.75 mmol) with triphenylphosphine 1c (0.131 g, 0.5 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(3-methoxyphenyl)-1,1,1-triphenyl-1,3-dihydro-1λ⁵-benzo[c][1,2]oxaphosphole 4j as a white solid (0.192 g, 81% yield).

$R_f$ (EtOAc): 0.50; $^1$H NMR (500 MHz, CDCl$_3$) δ 7.46 (t, J=7.2 Hz, 1H, H$_{ar}$), 7.40-7.38 (m, 6H, H$_{ar}$), 7.33-7.26 (m, 10H, H$_{ar}$), 7.23-7.16 (m, 2H, H$_{ar}$), 6.85-6.81 (m, 2H, H$_{ar}$), 6.74 (d, J=8.0 Hz, 1H, H$_{ar}$), 6.59 (s, 1H, H$_{ar}$), 5.66 (s, 1H, CH), 3.58 (s, 3H, OCH$_3$). $^{13}$C NMR (125 MHz, CDCl$_3$) δ 159.76, 154.33 (d, J=21.9 Hz), 146.01, 144.10, 143.26, 136.55 (d, J=14.5 Hz), 132.36, 131.43 (d, J=8.8 Hz), 129.10, 128.05, 127.50 (d, J=12.2 Hz), 127.27 (d, J=14.2 Hz), 124.86 (d, J=15.4 Hz), 120.12, 113.83, 112.05, 77.23, 55.20. $^{31}$P NMR (203 MHz, CDCl$_3$) δ −51.37 HRMS (ESI) calculated [M+H]$^+$ for C$_{32}$H$_{28}$O$_2$P: 475.1821. found: 475.1852. FTIR (cm$^{-1}$) 3678, 3015, 2361, 1647, 1462, 1215, 1052, 741, 667.

Example 11: Synthesis of 3-(3-Bromophenyl)-1,1,1-triphenyl-1,3-dihydro-1λ⁵-benzo[c][1,2] oxaphosphole (4k)

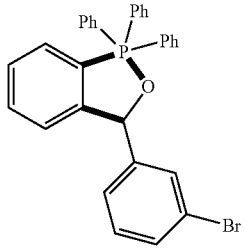

4k

Following the general procedure, treatment of 2-(trimethylsilyl)phenyl trifluoromethanesulfonate 1a (0.179 g, 146 μL, 0.60 mmol) and 3-bromobenzaldehyde 1b (0.139 g, 88 μL, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(3-bromophenyl)-1,1,1-triphenyl-1,3-dihydro-1λ⁵-benzo[c][1,2]oxaphosphole 4k as a white solid (0.194 g, 74% yield).

$R_f$ (EtOAc): 0.52; $^1$H NMR (400 MHz, CDCl$_3$) δ 7.48 (t, J=6.8 Hz, 1H, H$_{ar}$), 7.41-7.38 (m, 4H, H$_{ar}$), 7.36 (bs, 2H, H$_{ar}$), 7.33-7.29 (m, 10H, H$_{ar}$), 7.26-7.21 (m, 2H, H$_{ar}$), 7.16-7.08 (m, 3H, H$_{ar}$), 6.88 (dd, J$_1$=8.0 Hz, J$_2$=11.3 Hz, 1H, H$_{ar}$), 5.65 (s, 1H, CH). $^{13}$C NMR (100 MHz, CDCl$_3$) δ 153.53 (d, J=21.1 Hz), 146.78, 143.35, 142.32, 136.69 (d, J=14.5 Hz), 132.46 (d, J=2.9 Hz), 131.44 (d, J=8.9 Hz), 130.75, 130.28, 129.74, 128.31 (d, J=1.8 Hz), 127.61, 127.49, 126.22, 124.96 (d, J=15.2 Hz), 122.51, 76.45. $^{31}$P NMR (162 MHz, CDCl$_3$) δ −49.87 HRMS (ESI) calculated [M+H]$^+$ for C$_{31}$H$_{25}$BrOP: 523.0821. found: 523.0826. FTIR (cm$^{-1}$) 3894, 3860, 3743, 3678, 3619, 3012, 2362, 1836, 1741, 1693, 1647, 1516, 1479, 1429, 1217, 1184, 1065, 910, 742.

Example 12: Synthesis of 3-(3-Nitrophenyl)-1,1,1-triphenyl-1,3-dihydro-1λ⁵-benzo [c][1,2]oxaphosphole (4l)

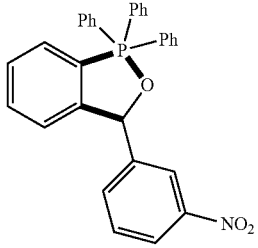

4l

Following the general procedure, treatment of 2-(trimethylsilyl)phenyl trifluoromethanesulfonate 1a (0.179 g, 146 μL, 0.6 mmol) and 3-nitrobenzaldehyde 1b (0.113 g, 0.75 mmol) with triphenylphosphine 1c (0.131 g, 0.5 mmol) in the presence of KF (0.070 g, 1.2 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(3-nitrophenyl)-1,1,1-triphenyl-1,3-dihydro-1λ⁵-benzo[c] [1,2]oxaphosphole 4l as a white solid (0.186 g, 76% yield).

$R_f$ (EtOAc): 0.47; $^1$H NMR (500 MHz, CDCl$_3$) δ 8.06 (d, J=8.0 Hz, 1H, H$_{ar}$), 7.96 (s, 1H, H$_{ar}$), 7.53-7.49 (m, 2H, H$_{ar}$), 7.40-7.34 (m, 16H, H$_{ar}$), 7.29-7.27 (m, 1H, H$_{ar}$), 7.24 (d, J=7.0 Hz, 1H, H$_{ar}$), 6.93 (dd, =8.2 Hz, J$_2$=11.3 Hz, 1H, H$_{ar}$), 5.81 (s, 1H, CH). $^{13}$C NMR (125 MHz, CDCl$_3$) δ 153.95 (d, J=20.6 Hz), 148.38, 146.98, 137.0 (d, J=14.77 Hz), 133.76, 132.65 (d, J=2.6 Hz), 131.30 (d, J=8.8 Hz), 129.12, 128.42, 127.85, 127.74, 127.64, 124.79 (d, J=15.2 Hz), 122.70, 122.32, 76.40. $^{31}$P NMR (203 MHz, CDCl$_3$) δ −49.49. HRMS (ESI) calculated [M+H]$^+$ for C$_{31}$H$_{25}$NO$_3$P: 490.1567. found: 490.1584. FTIR (cm$^{-1}$) 3743, 3060, 2361, 1580, 1529, 1349, 1064, 999, 693.

Example 13: Synthesis of 1,1,1-Triphenyl-3-(o-tolyl)-1,3-dihydro-1λ⁵-benzo[c][1,2]oxaphosphole (4m)

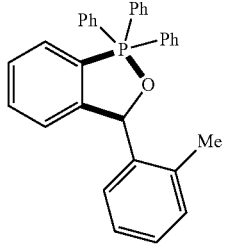

Following the general procedure, treatment of 2-(trimethylsilyl)phenyl trifluoromethanesulfonate 1a (0.179 g, 146 μL, 0.6 mmol) and 2-methylbenzaldehyde 1b (0.090 g, 87 μL, 0.75 mmol) with triphenylphosphine 1c (0.131 g, 0.5 mmol) in the presence of KF (0.070 g, 1.2 mmol) and 18-crown-6 (0.317 g, 1.2 mmol) in THF (3.0 mL) at −10° C. to rt for 12 h followed by flash column chromatography (Pet. ether/EtOAc=40/60) of the crude reaction mixture using silica gel afforded 1,1,1-triphenyl-3-(o-tolyl)-1,3-dihydro-1λ⁵-benzo[c][1,2]oxaphosphole 4m as a white solid (0.147 g, 64% yield).

$R_f$ (EtOAc): 0.42; ¹H NMR (500 MHz, CDCl₃) δ 7.45-7.37 (m, 7H, $H_{ar}$), 7.30-7.26 (m, 9H, $H_{ar}$), 7.24-7.20 (m, 1H, $H_{ar}$), 7.12-7.09 (m, 3H, $H_{ar}$), 7.06-7.03 (m, 1H, $H_{ar}$), 6.96 (d, J=7.36 Hz, 1H, $H_{ar}$), 6.89 (dd, (dd, $J_1$=8.3 Hz, $J_2$=10.8 Hz, 1H, $H_{ar}$), 5.32 (s, 1H, CH), 2.31 (s, 3H, CH₃). ¹³C NMR (125 MHz, CDCl₃) δ 154.74 (d, J=20.1 Hz), 141.98, 136.49 (d, J=14.3 Hz), 136.0, 132.18 (d, J=2.6 Hz), 131.64 (d, J=9.1 Hz), 130.28, 128.30, 128.14, 127.47 (d, J=12.3 Hz), 127.21, 127.14, 127.10, 126.23, 124.77 (d, J=15.0 Hz), 72.40, 19.74. ³¹P NMR (203 MHz, CDCl₃) δ −52.37. HRMS (ESI) calculated [M+H]⁺ for C₃₂H₂₈OP: 459.1872. found: 459.1873. FTIR (cm⁻¹) 3828, 3060, 2361, 1835, 1741, 1484, 1264, 1050, 742, 665.

Example 14: Synthesis of 3-(2-Fluorophenyl)-1,1,1-triphenyl-1,3-dihydro-1λ⁵-benzo[c][1,2]oxaphosphole (4n)

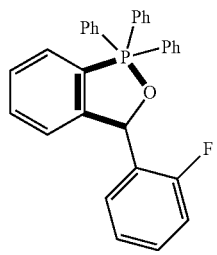

Following the general procedure, treatment of 2-(trimethylsilyl)phenyl trifluoromethanesulfonate 1a (0.179 g, 146 μL, 0.60 mmol) and 2-fluorobenzaldehyde 1b (0.093 g, 80 μL, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(2-fluorophenyl)-1,1,1-triphenyl-1,3-dihydro-1λ⁵-benzo[c][1,2]oxaphosphole 4n as a white solid (0.199 g, 86% yield).

$R_f$ (EtOAc): 0.49; ¹H NMR (400 MHz, CDCl₃) δ 7.49 (t, J=6.9 Hz, 1H, $H_{ar}$), 7.42-7.36 (m, 7H, $H_{ar}$), 7.33-7.29 (m, 9H, $H_{ar}$), 7.25-7.20 (m, 1H, $H_{ar}$), 7.18-7.13 (m, 1H, $H_{ar}$), 7.03 (t, J=9.7 Hz, 1H, $H_{ar}$), 6.91-6.60 (m, 3H, $H_{ar}$), 6.06 (s, 1H, CH). ¹³C NMR (100 MHz, CDCl₃) δ 160.65 (d, $J_{C-F}$=245.3 Hz), 153.91 (d, J=20.1 Hz), 143.60, 142.53, 136.66 (d, J=14.6 Hz), 132.60 (d, J=2.8 Hz), 131.73, 131.60, 131.44 (d, J=8.9 Hz), 129.42 (d, J=4.2 Hz), 128.67 (d, J=8.2 Hz), 128.23 (d, J=1.2 Hz), 127.61, 127.49, 127.30, 124.78 (dd, $J_1$=2.6 Hz, $J_2$=15.2 Hz), 124.23 (d, J=3.0 Hz), 115.10, 70.72. ³¹P NMR (162 MHz, CDCl₃) δ −51.40 HRMS (ESI) calculated [M+H]⁺ for C₃₁H₂₅FOP: 463.1622. found: 463.1646. FTIR (cm⁻¹) 3925, 3861, 3143, 3648, 3061, 3004, 2362, 1835, 1707, 1648, 1547, 1395, 1263, 1222, 1107, 1062, 808, 745, 667.

Example 15: Synthesis of 3-(3,4-Dichlorophenyl)-1,1,1-triphenyl-1,3-dihydro-1λ⁵-benzo[c][1,2]oxaphosphole (4o)

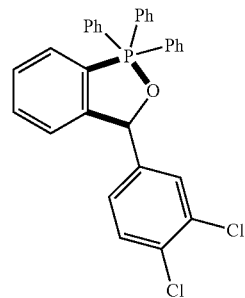

Following the general procedure, treatment of 2-(trimethylsilyl)phenyl trifluoromethanesulfonate 1a (0.179 g, 146 μL, 0.60 mmol) and 3,4-dichlorobenzaldehyde 1b (0.131 g, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(3,4-dichlorophenyl)-1,1,1-triphenyl-1,3-dihydro-1λ⁵-benzo[c][1,2]oxaphosphole 4o as a white solid (0.210 g, 82% yield).

$R_f$ (EtOAc): 0.48; ¹H NMR (400 MHz, CDCl₃) δ 7.52-7.48 (m, 1H, $H_{ar}$), 7.37-7.29 (m, 15H, $H_{ar}$), 7.28-7.22 (m, 3H, $H_{ar}$), 7.07 (bs, 1H, $H_{ar}$), 6.98 (dd, =1.9 Hz, $J_2$=8.3 Hz, 1H, $H_{ar}$), 6.87 (dd, =8.0 Hz, $J_2$=11.7 Hz, 1H, $H_{ar}$), 5.64 (s, 1H, CH). ¹³C NMR (100 MHz, CDCl₃) δ 153.18 (d, J=20.6 Hz), 144.96, 142.31, 136.85 (d, J=14.5 Hz), 132.60, 132.29, 131.43 (d, J=8.8 Hz), 131.02, 130.13, 129.68, 128.42, 127.64, (d, J=12.3 Hz), 126.88, 124.91 (d, J=14.5 Hz), 76.08. ³¹P NMR (162 MHz, CDCl₃) δ −49.64 HRMS (ESI) calculated [M+H]⁺ for C₃₁H₂₄Cl₂OP: 513.0936. found: 513.0968. FTIR (cm⁻¹) 3925, 3861, 2829, 3677, 3619. 3059, 2978, 2361, 1835, 1707, 1693, 1547, 1482, 1395, 1258, 1118, 894, 745, 716.

Example 16: Synthesis of 3-Mesityl-1,1,1-triphenyl-1,3-dihydro-1λ⁵-benzo[c][1,2] oxaphosphole (4p)

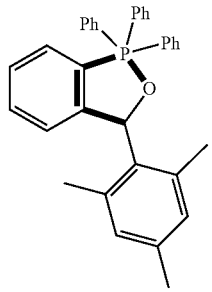

4p

Following the general procedure, treatment of 2-(trimethylsilyl)phenyl trifluoromethanesulfonate 1a (0.179 g, 146 μL, 0.60 mmol) and 2,4,6-trimethylbenzaldehyde 1b (0.111 g, 111 μL, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-mesityl-1,1,1-triphenyl-1,3-dihydro-1λ⁵-benzo[c][1,2]oxaphosphole 4p as a white solid (0.151 g, 62% yield).

$R_f$ (EtOAc): 0.29; ¹H NMR (400 MHz, CDCl₃) δ 7.49-7.41 (m, 7H, $H_{ar}$), 7.32 (bs, 9H, $H_{ar}$), 7.27-7.17 (m, 1H, $H_{ar}$), 7.07-7.03 (m, 2H, $H_{ar}$), 6.76 (bs, 2H, $H_{ar}$), 5.62 (s, 1H, CH), 2.23 (s, 3H, $CH_3$), 2.09 (s, 3H, $CH_3$), 1.86 (s, 3H, $CH_3$). ¹³C NMR (100 MHz, CDCl₃) δ 155.41 (d, J=19.4 Hz), 141.84, 140.79, 138.04, 137.38, 136.90, 136.49 (d, J=13.8 Hz), 134.05, 132.10, 131.71 (d, J=8.7 Hz), 130.76, 128.87, 128.33, 127.52 (d, J=12.3 Hz), 126.81 (d, J=14.3 Hz), 123.47 (d, J=14.6 Hz), 70.45, 21.13, 20.96, 20.53. ³¹P NMR (162 MHz, CDCl₃) δ −49.31 HRMS (ESI) calculated [M+H]⁺ for $C_{34}H_{32}OP$: 487.2185. found: 487.2185. FTIR (cm⁻¹) 3759, 3672, 3063, 3013, 2926, 2855, 1891, 1626, 1517, 1438, 1342, 1273, 1071, 987, 839, 744.

Example 17: Synthesis of 3-(Naphthalen-2-yl)-1,1,1-triphenyl-1,3-dihydro-1λ⁵-benzo [c][1,2]oxaphosphole (4q)

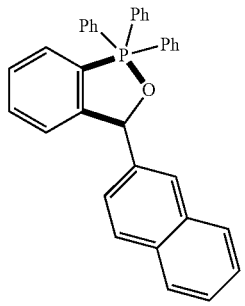

4q

Following the general procedure, treatment of 2-(trimethylsilyl)phenyl trifluoromethanesulfonate 1a (0.179 g, 146 μL, 0.60 mmol) and 2-naphthaldehyde 1b (0.117 g, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(naphthalen-2-yl)-1,1,1-triphenyl-1,3-dihydro-1λ⁵-benzo[c][1,2] oxaphosphole 4q as a white solid (0.195 g, 79% yield).

$R_f$ (EtOAc): 0.54; ¹H NMR (500 MHz, CDCl₃) δ 7.65-7.64 (m, 1H, $H_{ar}$), 7.60 (d, J=8.5 Hz, 1H, $H_{ar}$), 7.54-7.53 (m, 1H, $H_{ar}$), 7.43 (s, 1H, $H_{ar}$), 7.36-7.28 (m, 9H, $H_{ar}$), 7.20 (bs, 9H, $H_{ar}$), 7.15-7.07 (m, 3H, $H_{ar}$), 6.74 (d, J=10.3 Hz, 2H, $H_{ar}$), 5.68 (s, 1H, CH). ¹³C NMR (125 MHz, CDCl₃) δ 154.31 (d, J=21.9 Hz), 143.96, 143.10, 141.63, 136.57 (d, J=14.5 Hz), 133.37, 132.99, 132.30 (d, J=2.1 Hz), 132.24, 131.59 (d, J=8.9 Hz), 128.63 (d, J=12.1 Hz), 128.12, 128.03 (d, J=6.8 Hz), 127.66, 127.50 (d, J=12.3 Hz), 127.28, 126.92, 125.81 (d, J=8.9 Hz), 125.60, 125.02 (d, J=15.5 Hz), 77.16 (merged with the CDCl₃ peak). ³¹P NMR (203 MHz, CDCl₃) δ −49.43 HRMS (ESI) calculated [M+H]⁺ for $C_{35}H_{28}OP$: 495.1872. found: 495.1876. FTIR (cm⁻¹) 3843, 3648, 3590, 3063, 2926, 2321, 1635, 1607, 1514, 1432, 1292, 1185, 1083, 889, 815, 751, 696.

Example 18: Synthesis of 1,1,1-Triphenyl-3-(pyren-4-yl)-1,3-dihydro-1λ⁵-benzo[c][1,2]oxaphosphole (4r)

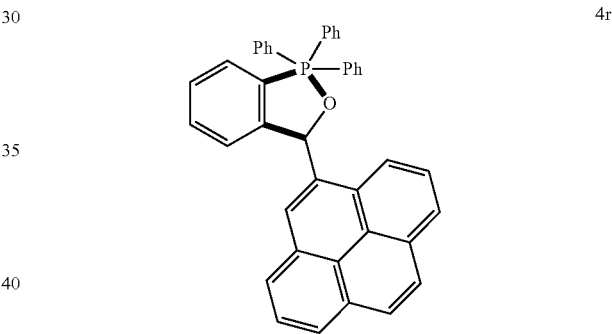

4r

Following the general procedure, treatment of 2-(trimethylsilyl)phenyl trifluoromethanesulfonate 1a (0.179 g, 146 μL, 0.60 mmol) and pyrene-4-carbaldehyde 1b (0.173 g, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 1,1,1-triphenyl-3-(pyren-4-yl)-1,3-dihydro-1λ⁵-benzo[c][1,2]oxaphosphole 4r as a yellow solid (0.201 g, 71% yield).

$R_f$ (EtOAc): 0.53; ¹H NMR (400 MHz, CDCl₃) δ 8.46 (d, J=9.4 Hz, 1H, $H_{ar}$), 8.19 (d, J=7.6 Hz, 2H, $H_{ar}$), 8.11 (d, J=9.4 Hz, 1H, $H_{ar}$), 8.07-8.04 (m, 3H, $H_{ar}$), 8.00 (d, J 7.7 Hz, 1H, $H_{ar}$), 7.75 (d, J=8.0 Hz, 1H, $H_{ar}$), 7.60-7.50 (m, 6H, $H_{ar}$), 7.40-7.34 (m, 10H, $H_{ar}$), 7.29-7.22 (m, 2H, $H_{ar}$), 7.04 (dd, =8.3 Hz, $J_2$=11.2 Hz, 1H, $H_{ar}$), 6.77 (s, 1H, CH). ¹³C NMR (100 MHz, CDCl₃) δ 154.84 (d, J=21.0 Hz), 143.60, 142.55, 137.94, 136.72 (d, J=14.4 Hz), 132.33 (d, J=2.7 Hz), 132.22, 132.12, 131.62 (d, J=8.9 Hz), 131.46, 130.80, 130.57, 129.46, 128.93, 128.66, 128.54, 128.25, 127.56 (d, J=12.6 Hz), 127.44, 127.04, 125.96, 125.82, 125.23 (d, J=15.9 Hz), 124.92 (d, J=16.8 Hz), 123.60, 73.01. ³¹P NMR (162 MHz, CDCl₃) δ −50.44 HRMS (ESI) calculated

[M+H]⁺ for $C_{41}H_{30}OP$: 569.2029. found: 569.2029. FTIR (cm⁻¹) 2985, 1733, 1438, 1372, 1241, 1194, 1045, 939, 847, 754, 696, 654, 639.

Example 19: Synthesis of 3-(Benzofuran-2-yl)-1,1,1-triphenyl-1,3-dihydro-1λ⁵-benzo [c] [1,2] oxaphosphole (4s)

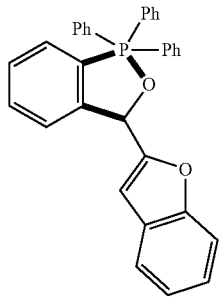

4s

Following the general procedure, treatment of 2-(trimethylsilyl)phenyl trifluoromethanesulfonate 1a (0.179 g, 146 μL, 0.60 mmol) and benzofuran-2-carbaldehyde 1b (0.110 g, 91 μL, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(benzofuran-2-yl)-1,1,1-triphenyl-1,3-dihydro-1λ⁵-benzo[c][1,2] oxaphosphole 4s as a white solid (0.203 g, 83% yield).

$R_f$ (EtOAc): 0.36; ¹H NMR (400 MHz, CDCl₃) δ 7.65-7.63 (m, 1H, $H_{ar}$), 7.60-7.56 (m, 1H, $H_{ar}$), 7.52-7.43 (m, 8H, $H_{ar}$), 7.39-7.31 (m, 9H, $H_{ar}$), 7.29-7.25 (m, 2H, $H_{ar}$), 7.23-7.20 (m, 1H, $H_{ar}$), 6.83 (dd, $J_1$=8.0 Hz, $J_2$=11.3 Hz, 1H), 6.35 (s, 1H), 5.92 (s, 1H). ¹³C NMR (100 MHz, CDCl₃) δ 159.23, 155.21, 150.81 (d, J=20.4 Hz), 143.66, 142.60, 136.88 (d, J=14.3 Hz), 132.52 (d, J=3.0 Hz), 131.69 (d, J=9.0 Hz), 128.43, 128.26 (d, J=2.2 Hz), 127.99 (d, J=14.2 Hz), 127.46 (d, J=12.5 Hz), 124.82 (d, J=15.1 Hz), 123.70, 122.47, 120.92, 111.91, 103.94, 70.49. ³¹P NMR (162 MHz, CDCl₃) δ −43.56 HRMS (ESI) calculated [M+H]⁺ for $C_{33}H_{26}OP$: 485.1665. found: 485.1674. FTIR (cm⁻¹) 3893, 3843, 3743, 3678, 3648, 3619, 3015, 2396, 1741, 1693, 1647, 1516, 1461, 1216, 1117, 741, 668.

Example 20: Synthesis of 1,1,1-Triphenyl-3-(thiophen-2-yl)-1,3-dihydro-1λ⁵-benzo [c][1,2] oxaphosphole (4t)

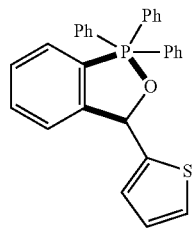

4t

Following the general procedure, treatment of 2-(trimethylsilyl)phenyl trifluoromethanesulfonate 1a (0.179 g, 146 μL, 0.60 mmol) and thiophene-2-carbaldehyde 1b (0.084 g, 70 μL, 0.75 mmol) with triphenylphosphine 1c (0.131 g, 0.50 mmol) in the presence of KF (0.070 g, 1.2 mmol) and 18-crown-6 (0.317 g, 1.2 mmol) in THF (3.0 mL) at −10° C. to rt for 12 h followed by flash column chromatography (Pet. ether/EtOAc=40/60) of the crude reaction mixture using silica gel afforded 1,1,1-triphenyl-3-(thiophen-2-yl)-1,3-dihydro-1λ⁵-benzo[c][1,2]oxaphosphole 4t as a white solid (0.149 g, 66% yield).

$R_f$ (EtOAc): 0.39 ¹H NMR (500 MHz, CDCl₃) δ 7.52 (t, J=6.2 Hz, 1H, $H_{ar}$), 7.44-7.41 (m, 6H, $H_{ar}$), 7.39-7.34 (m, 10H, $H_{ar}$), 7.27-7.23 (m, 1H, $H_{ar}$), 7.20 (d, J=4.7 Hz, 1H, $H_{ar}$), 7.02 (s, 1H, $H_{ar}$), 6.94 (bs, 1H), 6.84 (t, J=8.6 Hz, 1H, $H_{ar}$), 5.83 (s, 1H, CH). ¹³C NMR (125 MHz, CDCl₃) δ 153.78 (d, J=20.6 Hz), 148.64, 143.40, 142.55, 136.36 (d, J=14.4 Hz), 132.30 (d, J=2.8 Hz), 131.56 (d, J=9.1 Hz), 128.11, 127.66, 127.54, 127.38 (d, J=12.1 Hz), 126.09, 125.16 (d, J=11.9 Hz), 124.75 (d, J=15.7 Hz), 71.95. ³¹P NMR (203 MHz, CDCl₃) δ −51.66 HRMS (ESI) calculated [M+H]⁺ for $C_{29}H_{24}OPS$: 451.1280. found: 451.1279. FTIR (cm⁻¹) 3894, 3861, 3678, 3648, 3619, 3011, 2873, 2362, 1836, 1741, 1693, 1647, 1464, 1216, 1116. 1030. 948, 741, 656.

Example 21: Synthesis of 3-Cyclohexyl-1,1,1-triphenyl-1,3-dihydro-1λ⁵-benzo[c][1,2]oxaphosphole (4u)

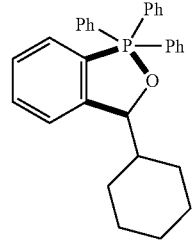

4u

Following the general procedure, treatment of 2-(trimethylsilyl)phenyl trifluoromethanesulfonate 1a (0.179 g, 146 μL, 0.60 mmol) and cyclohexanecarbaldehyde 1b (0.084 g, 91 μL, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-cyclohexyl-1,1,1-triphenyl-1,3-dihydro-1λ⁵-benzo[c][1,2]oxaphosphole 4u as a white solid (0.191 g, 85% yield).

$R_f$ (EtOAc): 0.33; ¹H NMR (500 MHz, CDCl₃) δ 7.55 (s, 2H, $H_{ar}$), 7.38-7.36 (m, 6H, $H_{ar}$), 7.30-7.26 (m, 9H, $H_{ar}$), 7.24 (bs, 1H, $H_{ar}$), 6.91-6.89 (m, 1H, $H_{ar}$), 4.64 (s, 1H, CH), 1.75 (bs, 2H), 1.63 (bs, 3H), 1.38-1.25 (m, 3H), 1.10-1.06 (m, 2H), 0.84-0.83 (m, 1H). ¹³C NMR (125 MHz, CDCl₃) δ 154.05 (d, J=24.2 Hz), 144.80, 143.96, 136.61 (d, J=14.5 Hz), 131.59 (d, J=8.8 Hz), 129.95, 127.64, 127.10 (d, J=12.1 Hz), 126.77 (d, J=14.1 Hz), 123.38 (d, J=15.7 Hz), 77.84, 44.07, 30.69, 27.18, 26.87, 26.65, 26.54. ³¹P NMR (203 MHz, CDCl₃) δ −52.53 HRMS (ESI) calculated [M+H]⁺ for $C_{31}H_{32}OP$: 451.2185. found: 451.2185. FTIR (cm⁻¹) 3840,

Example 22: Synthesis of 3-Nonyl-1,1,1-triphenyl-1,3-dihydro-1λ⁵-benzo[c][1,2] oxaphosphole (4v)

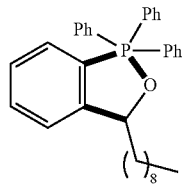

Following the general procedure, treatment of 2-(trimethylsilyl)phenyl trifluoromethanesulfonate 1a (0.179 g, 146 µL, 0.60 mmol) and decanal 1b (0.117 g, 141 µL, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-nonyl-1,1,1-triphenyl-1,3-dihydro-1λ⁵-benzo[c][1,2]oxaphosphole 4v as a white solid (0.146 g, 59% yield).

$R_f$ (EtOAc): 0.38; ¹H NMR (400 MHz, CDCl$_3$) δ 7.57-7.53 (m, 1H, H$_{ar}$), 7.51-7.49 (m, 1H, H$_{ar}$), 7.35-7.33 (m, 4H, H$_{ar}$), 7.31-7.25 (m, 11H, H$_{ar}$), 7.22-7.18 (m, 1H, H$_{ar}$), 6.74 (dd, J$_1$=8.2 Hz, J$_2$=11.3 Hz, 1H, H$_{ar}$), 4.78 (dd, J$_1$=4.1 Hz, J$_2$=6.0 Hz, 1H, CH), 1.77-1.72 (m, 1H), 1.61-1.56 (m, 1H), 1.39-1.28 (m, 4H), 1.23 (bs, 4H), 1.14 (bs, 6H), 0.90 (t, J=6.8 Hz, 3H, CH$_3$). NMR (100 MHz, CDCl$_3$) δ 155.06 (d, J=22.8 Hz), 143.32, 142.27, 136.62 (d, J=14.5 Hz), 132.26 (d, J=2.7 Hz), 131.81 (d, J=8.9 Hz), 128.27, 127.42 (d, J=12.3 Hz), 126.98 (d, J=14.1 Hz), 123.76 (d, J=15.4 Hz), 73.18 (d, J=2.4 Hz), 37.13, 32.01, 29.91, 29.61, 29.56, 29.40, 25.21, 22.79, 14.24. ³¹P NMR (162 MHz, CDCl$_3$) δ −46.43 HRMS (ESI) calculated [M+H]⁺ for C$_{34}$H$_{40}$OP: 495.2811. found: 495.2810. FTIR (cm⁻¹) 3842, 3743, 3616, 1063, 2927. 2855. 2360. 1742. 16932, 1648. 1488, 1436, 1293, 1180, 1117, 1081, 1003, 836, 744, 697.

Example 23: Synthesis of 1,1,1-Triphenyl-3-vinyl-1,3-dihydro-1λ⁵-benzo[c][1,2] oxaphosphole (4w)

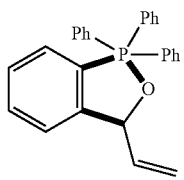

Following the general procedure, treatment of 2-(trimethylsilyl)phenyl trifluoromethanesulfonate 1a (0.179 g, 146 µL, 0.60 mmol) and acrylaldehyde 1b (0.042 g, 50 µL, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 24 h followed by flash column chromatography (Pet. ether/EtOAc=40/60) of the crude reaction mixture using silica gel afforded 1, 1,1-triphenyl-3-vinyl-1,3-dihydro-1λ⁵-benzo[c][1,2]oxaphosphole 4w as a yellow solid (0.132 g, 67% yield).

$R_f$ (EtOAc): 0.21; ¹H NMR (400 MHz, CDCl$_3$) δ 7.60-7.56 (m, 1H, H$_{ar}$), 7.50 (d, J=7.2 Hz, 1H, H$_{ar}$), 7.38-7.36 (m, 4H, H$_{ar}$), 7.34-7.27 (m, 11H, H$_{ar}$), 7.25-7.22 (m, 1H, H$_{ar}$), 6.73 (dd, J$_1$=8.1 Hz, J$_2$=10.9 Hz, 1H, H$_{ar}$), 5.92-5.83 (m, 1H), 5.24 (d, J=17.0 Hz, 1H), 5.16-5.14 (m, 2H). ¹³C NMR (100 MHz, CDCl$_3$) δ 152.81 (d, J=22.7 Hz), 144.33, 143.28, 139.60, 136.68 (d, J=14.5 Hz), 132.20 (d, J=3.1 Hz), 131.52 (d, J=9.0 Hz), 127.99 (d, J=2.1 Hz), 127.36, 127.24, 124.34 (d, J=15.5 Hz), 116.10, 75.95. ³¹P NMR (162 MHz, CDCl$_3$) δ −51.78 HRMS (ESI) calculated [M+H]⁺ for C$_{27}$H$_{24}$OP: 395.1559. found: 395.1559. FTIR (cm⁻¹) 3925, 3861, 3743, 3619, 3060, 2980, 2320, 1964, 1693, 1612, 1469, 1435, 1369, 1251, 1182, 1039, 938, 803, 692.

Example 24: Synthesis of 1,1,1-Triphenyl-3-styryl-1,3-dihydro-1λ⁵-benzo[c][1,2] oxaphosphole (4x)

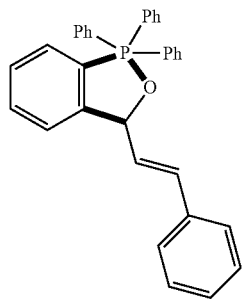

Following the general procedure, treatment of 2-(trimethylsilyl)phenyl trifluoromethanesulfonate 1a (0.179 g, 146 µL, 0.60 mmol) and trans cinnamaldehyde 1b (0.099 g, 94 µL, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 24 h followed by flash column chromatography (Pet. ether/EtOAc=40/60) of the crude reaction mixture using silica gel afforded 1,1,1-triphenyl-3-styryl-1,3-dihydro-1λ⁵-benzo[c][1,2]oxaphosphole 4x as a yellow solid (0.156 g, 66% yield).

$R_f$ (EtOAc): 0.30; ¹H NMR (400 MHz, CDCl$_3$) δ 7.60-7.53 (m, 2H, H$_{ar}$), 7.40-7.37 (m, 4H, H$_{ar}$), 7.53-7.29 (m, 15H, H$_{ar}$), 7.27-7.24 (m, 2H, H$_{ar}$), 6.75 (dd, =8.2 Hz, J$_2$=10.8 Hz, 1H), 6.49 (d, J=15.6 Hz, 1H), 6.23 (dd, J$_1$=7.0 Hz, J$_2$=15.7 Hz, 1H), 5.35 (s, 1H, CH). ¹³C NMR (100 MHz, CDCl$_3$) δ 153.17 (d, J=22.4 Hz), 144.59, 143.53, 137.23, 136.84 (d, J=14.6 Hz), 132.28 (d, J=2.9 Hz), 131.59 (d, J=8.9 Hz), 131.18 (d, J=9.9 Hz), 129.00, 128.45, 128.03, (d, J=2.0 Hz), 127.66, 127.58, 127.39 (d, J=12.3 Hz), 126.62, 124.45 (d, J=15.4 Hz), 75.35. ³¹P NMR (162 MHz, CDCl$_3$) δ −51.56 HRMS (ESI) calculated [M+H]⁺ for C$_{33}$H$_{28}$OP: 471.1872. found: 471.1896. FTIR (cm⁻¹) 3829. 3743, 3678, 3648. 3061. 2980, 2320. 1738, 1647, 1609, 1469. 1433, 1370, 1250, 1195, 1112, 1039, 986, 872, 801, 742.

Example 25: Synthesis of 3-(4-Methoxystyryl)-1,1,1-triphenyl-1,3-dihydro-1λ⁵-benzo[c][1,2] oxaphosphole (4y)

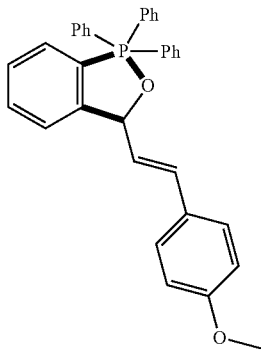

4y

Following the general procedure, treatment of 2-(trimethylsilyl)phenyl trifluoromethanesulfonate 1a (0.179 g, 146 µL, 0.60 mmol) and (E)-3-(4-methoxyphenyl)acrylaldehyde 1b (0.122 g, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 24 h followed by flash column chromatography (Pet. ether/EtOAc=40/60) of the crude reaction mixture using silica gel afforded 3-(4-methoxystyryl)-1,1,1-triphenyl-1,3-dihydro-1λ⁵-benzo[c][1,2] oxaphosphole 4y as a yellow solid (0.153 g, 61% yield).

$R_f$ (EtOAc): 0.27; ¹H NMR (400 MHz, CDCl₃) δ 7.73-7.64 (m, 1H, $H_{ar}$), 7.56-7.47 (m, 3H, $H_{ar}$), 7.36-7.33 (m, 4H, $H_{ar}$), 7.31-7.26 (m, 9H, $H_{ar}$), 7.22 (d, J=7.9 Hz, 3H, $H_{ar}$), 6.82 (d, J=8.5 Hz, 2H, $H_{ar}$), 6.71 (t, J=9.1 Hz, 1H, $H_{ar}$), 6.41 (d, J=15.8 Hz, 1H), 6.05 (d, $J_1$=8.5 Hz, $J_2$=15.7 Hz, 1H), 5.27 (d, J=7.1 Hz, 1H, CH), 3.79 (s, 3H, CH₃). ¹³C NMR (100 MHz, CDCl₃) δ 159.04, 153.35 (d, J=22.7 Hz), 144.59, 143.54, 136.75 (d, J=14.5 Hz), 132.22, 132.12, 132.04, 131.59 (d, J=8.8 Hz), 130.85, 130.00, 128.93, 127.98 (d, J=1.8 Hz), 127.75, 127.35, (d, J=12.4 Hz), 124.47 (d, J=15.4 Hz), 113.86, 75.46, 55.31. ³¹P NMR (162 MHz, CDCl₃) δ −51.80 HRMS (ESI) calculated [M+H]⁺ for C₃₄H₃₀OP: 501.1978. found: 501.1995.

FTIR (cm¹) 3861, 3744, 3678, 3619, 3060, 2981, 1736, 1647. 1608, 1469, 1434, 1370, 1249, 119 5, 1113, 1079, 986, 872, 833, 745.

Example 26: Synthesis of 3-(4-Chlorophenyl)-5,6-dimethyl-1,1,1-triphenyl-1,3-dihydro-1λ⁵ benzo[c][1,2]oxaphosphole (4z)

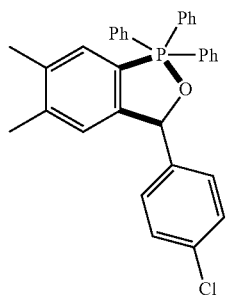

4z

Following the general procedure, treatment of 4,5-dimethyl-2-(trimethylsilyl)phenyl trifluoromethanesulfonate 1a (0.196 g, 0.60 mmol) and 4-chlorobenzaldehyde 1b (0.105 g, 0.75 mmol) with triphenylphosphine 1c (0.131 g, 0.50 mmol) in the presence of KF (0.070 g, 1.2 mmol) and 18-crown-6 (0.317 g, 1.2 mmol) in THF (3.0 mL) at −10° C. to rt for 12 h followed by flash column chromatography (Pet. ether/EtOAc=40/60) of the crude reaction mixture using silica gel afforded 3-(4-chlorophenyl)-5,6-dimethyl-1,1,1-triphenyl-1,3-dihydro-1λ⁵-benzo[c][1,2]oxaphosphole 4z as a white solid (0.163 g, 64% yield).

$R_f$ (EtOAc): 0.39; ¹H NMR (400 MHz, CDCl₃) δ 7.42-7.37 (m, 6H), 7.32-7.26 (m, 9H), 7.22 (d, J=8.1 Hz, 2H), 7.07 (d, J=7.8 Hz, 2H), 6.98 (bs, 1H), 6.59 (d, J=11.3 Hz, 1H), 5.61 (s, 1H, CH), 2.27 (s, 3H), 2.13 (s, 3H). ¹³C NMR (100 MHz, CDCl₃) δ 151.96 (d, J=21.2 Hz), 144.07, 143.33, 143.01, 142.08 (d, J=3.1 Hz), 137.26 (d, J=14.9 Hz), 135.96 (d, J=14.8 Hz), 132.72, 131.35 (d, J=8.6 Hz), 129.06, 128.60, 127.99 (d, J=1.7 Hz), 127.38 (d, J=12.3 Hz), 125.84 (d, J=16.2 Hz), 76.24, 20.15, 20.11. ³¹P NMR (162 MHz, CDCl₃) δ −51.37 HRMS (ESI) calculated [M+H]⁺ for C₃₃H₂₉ClOP: 507.1639. found: 507.1643. FTIR (cm⁻¹) 3925, 3861, 3829, 3648, 3566, 3058, 2979, 2360, 1835, 1741, 1707, 1647, 1485, 1436, 1265, 1225, 1081, 1018, 810, 745, 662.

Example 27: Synthesis of 3-(4-Chlorophenyl)-5,6-difluoro-1,1,1-triphenyl-1,3-dihydro-1λ⁵-benzo[c][1,2] oxaphosphole (4aa)

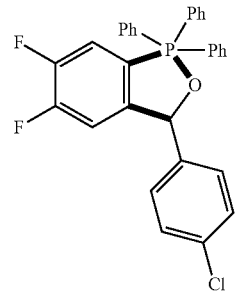

4aa

Following the general procedure, treatment of 4,5-difluoro-2-(trimethylsilyl)phenyl trifluoromethanesulfonate 1a (0.201 g, 0.60 mmol) and 4-chlorobenzaldehyde 1b (0.105 g, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(4-chlorophenyl)-5,6-difluoro-1,1,1-triphenyl-1,3-dihydro-1λ⁵-benzo[c][1,2]oxaphosphole 4aa as a white solid (0.193 g, 75% yield).

$R_f$ (EtOAc): 0.48; ¹H NMR (400 MHz, CDCl₃) δ 7.37-7.32 (m, 15H, $H_{ar}$), 7.22 (d, J=8.0 Hz, 2H, $H_{ar}$), 7.04 (d, J=8.0 Hz, 2H, $H_{ar}$), 6.93 (t, J=6.9 Hz, 1H, $H_{ar}$), 6.62-6.55 (m, 1H, $H_{ar}$), 5.43 (s, 1H, CH). ¹³C NMR (100 MHz, CDCl₃) δ 153.33 (d, J=259.8 Hz), 153.20 (d, J=257.5 Hz), 151.16-150.81 (m), 150.62 (d, J=5.4 Hz), 148.51 (d, $J_1$=12.9 Hz, $J_2$=22.0 Hz), 142.99, 141.78, 133.46, 131.39 (d, J=9.0 Hz), 129.03, 128.62 (d, J=7.2 Hz), 127.93, 127.70 (d, J=12.5 Hz), 124.57 (t, J=18.7 Hz), 113.13 (t, J=18.4 Hz), 75.45. ³¹P NMR (162 MHz, CDCl₃) δ −51.78 HRMS (ESI) calculated [M+H]⁺ for C₃₁H₂₃ClF₂OP: 515.1138. found: 515.1165.

FTIR (cm$^{-1}$) 3894, 3861, 3744, 3678, 2928, 2361, 1741, 1693, 1647, 1614, 1516, 1488, 1430, 1293, 1215, 1084, 1006, 898, 742.

Example 28: Synthesis of 3-(4-Chlorophenyl)-1,1,1-triphenyl-1,3-dihydro-1λ$^5$-[1,3]dioxolo[4',5':4,5]benzo[1,2-c][1,2]oxaphosphole (4ab)

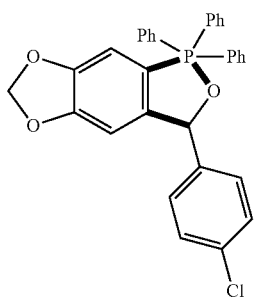

4ab

Following the general procedure, treatment of 6-(trimethylsilyl)benzo[d][1,3]dioxol-5-yl trifluoromethanesulfonate 1a (0.206 g, 0.60 mmol) and 4-chlorobenzaldehyde 1b (0.105 g, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(4-chlorophenyl)-1,1,1-triphenyl-1,3-dihydro-1λ$^5$-[1,3]dioxolo[4',5':4,5]benzo[1,2-c][1,2]oxaphosphole 4ab as a white solid (0.201 g, 77% yield).

$R_f$ (EtOAc): 0.32; $^1$H NMR (400 MHz, CDCl$_3$) δ 7.40-7.26 (m, 6H, H$_{ar}$), 7.32 (bs, 9H, H$_{ar}$), 7.22-7.20 (m, 2H, H$_{ar}$), 7.06-7.04 (m, 2H, H$_{ar}$), 6.59 (bs, 1H, H$_{ar}$), 6.21-6.17 (m, 1H, H$_{ar}$), 5.97 (d, J=6.2 Hz, 2H, CH$_2$), 5.50 (s, 1H, CH). $^{13}$C NMR (100 MHz, CDCl$_3$) δ 151.94, 150.23 (d, J=23.0 Hz), 147.84 (d, J=22.4 Hz), 143.31, 142.73, 142.25, 133.02, 131.41 (d, J=8.9 Hz), 129.10, 128.37 (d, J=9.3 Hz), 127.57 (d, J=12.5 Hz), 120.74, 119.34, 114.56 (d, J=19.3 Hz), 104.85 (d, J=19.1 Hz), 102.28, 76.16. $^{31}$P NMR (162 MHz, CDCl$_3$) δ −49.02 HRMS (ESI) calculated [M+H]$^+$ for C$_{32}$H$_{25}$ClO$_3$P: 523.1224. found: 523.1228. FTIR (cm$^{-1}$) 3829, 3744, 3619, 3061, 2981, 2899, 1736, 1609, 1469, 1432, 1250, 1079, 986, 832, 745, 661.

Example 29: Synthesis of 3-(4-Chlorophenyl)-1,1,1-triphenyl-3,5,6,7-tetrahydro-1H-1λ$^5$-indeno[5,6-c][1,2]oxaphosphole (4ac)

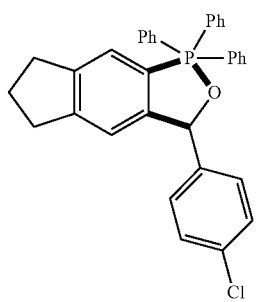

4ac

Following the general procedure, treatment of 6-(trimethylsilyl)-2,3-dihydro-1H-inden-5-yl trifluoromethanesulfonate 1a (0.201 g, 0.60 mmol) and 4-chlorobenzaldehyde 1b (0.105 g, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(4-chlorophenyl)-1,1,1-triphenyl-3,5,6,7-tetrahydro-1H-1λ$^5$-indeno[5,6-c][1,2]oxaphosphole 4ac as a white solid (0.204 g, 79% yield).

$R_f$ (EtOAc): 0.43; $^1$H NMR (400 MHz, CDCl$_3$) δ 7.42-7.37 (m, 6H, H$_{ar}$), 7.31-7.27 (m, 9H, H$_{ar}$), 7.21 (d, J=8.3 Hz, 2H, H$_{ar}$), 7.08 (d, J=8.4 Hz, 2H, H$_{ar}$), 7.03 (b s, 1H, H$_{ar}$), 6.69 (d, J=11.3 Hz, 1H, H$_{ar}$), 5.59 (s, 1H, CH), 2.94-2.83 (m, 2H, CH$_2$), 2.77 (t, J=7.3 Hz, 2H, CH$_2$), 2.12-2.04 (m, 2H, CH$_2$). $^{13}$C NMR (100 MHz, CDCl$_3$) δ 152.89 (d, J=22.5 Hz), 150.18 (d, J=2.9 Hz), 144.23, 144.19, 144.08, 143.42, 143.12, 132.74, 131.84 (d, J=15.4 Hz), 131.34 (d, J=8.9 Hz), 129.10, 128.29, 127.96 (d, J=1.8 Hz), 127.39 (d, J=12.3 Hz), 120.53 (d, J=17.0 Hz), 76.37, 32.71, 32.47, 25.85. $^{31}$P NMR (162 MHz, CDCl$_3$) δ −51.78 HRMS (ESI) calculated [M+H]$^+$ for C$_{34}$H$_{29}$ClOP: 519.1639. found: 519.1638. FTIR (cm$^{-1}$) 3893, 3843, 3743, 3565, 3059, 3008, 2361, 1845, 1740, 1693, 1546, 1485, 1436, 1398, 1268, 1195, 1111, 1034, 803, 694, 633.

Example 30: Synthesis of 1-(4-Chlorophenyl)-3,3,3-triphenyl-1,3-dihydro-3λ$^5$-naphtho[2,1-c][1,2] oxaphosphole (4ad)

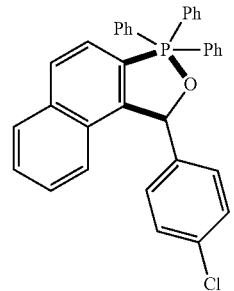

4ad

Following the general procedure, treatment of 2-(trimethylsilyl)naphthalen-1-yl trifluoromethanesulfonate 1a (0.209 g, 0.60 mmol) and 4-chlorobenzaldehyde 1b (0.105 g, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 1-(4-chlorophenyl)-3,3,3-triphenyl-1,3-dihydro-3λ$^5$-naphtho[2,1-c][1,2]oxaphosphole 4ad as a white solid (0.181 g, 68% yield).

$R_f$ (EtOAc): 0.45; $^1$H NMR (400 MHz, CDCl$_3$) δ 7.81 (d, J=8.2 Hz, 1H, H$_{ar}$), 7.71 (d, J=8.3 Hz, 1H, H$_{ar}$), 7.50-7.42 (m, 8H, H$_{ar}$), 7.36 (d, J=8.2 Hz, 2H, H$_{ar}$), 7.27-7.22 (m, 10H, H$_{ar}$), 7.19 (d, J=7.5 Hz, 1H, H$_{ar}$), 7.05 (d, J=8.6 Hz,

1H, H$_{ar}$), 6.91 (t, J=7.3 Hz, 1H, H$_{ar}$), 6.23 (d, J=8.2 Hz, 1H, H$_{ar}$). $^{13}$C NMR (100 MHz, CDCl$_3$) δ 147.85, 147.00, 142.93, 141.47 (d, J=2.0 Hz), 134.05 (d, J=8.0 Hz), 133.55, 132.21 (d, J=11.3 Hz), 131.83 (d, J=9.9 Hz), 131.46, 128.79, 128.56, 128.32, 127.47 (d, J=12.1 Hz), 125.29, 124.81, 121.00, 74.08. $^{31}$P NMR (162 MHz, CDCl$_3$) δ −49.36 HRMS (ESI) calculated [M+H]$^+$ for C$_{35}$H$_{27}$ClOP: 529.1483. found: 529.1483. FTIR (cm$^{-1}$) 3894, 3648, 3619, 3011, 2362, 1836, 1707, 1648, 1646, 1467, 1429, 1282, 1217, 1009, 743, 668.

Example 31: Synthesis of 3-(4-Chlorophenyl)-5-methyl-1,1,1-triphenyl-1,3-dihydro-1λ$^5$-benzo[c][1,2] oxaphosphole & 3-(4-Chlorophenyl)-6-methyl-1,1,1-triphenyl-1,3-dihydro-1λ$^5$-benzo[c][1,2] oxaphosphole (4ae & 4ae')

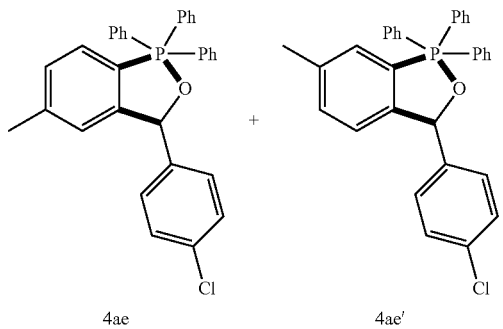

4ae      4ae'

Following the general procedure, treatment of 5-methyl-2-(trimethylsilyl)phenyl trifluoromethanesulfonate 1a (0.189 g, 0.60 mmol) and 4-chlorobenzaldehyde 1b (0.105 g, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(4-chlorophenyl)-5-methyl-1,1,1-triphenyl-1,3-dihydro-1λ$^5$-benzo[c] [1,2] oxaphosphole 4ae and 3-(4-chlorophenyl)-6-methyl-1,1,1-triphenyl-1,3-dihydro-1λ$^5$-benzo[c][1,2]oxaphosphole 4ae' as inseparable mixture of regioisomers in 1:1 ratio as a white solid (0.229 g, 93% yield, regioisomeric ratio was determined by $^1$H NMR analysis of crude reaction mixture).

R$_f$ (EtOAc): 0.45; $^1$H NMR (500 MHz, CDCl$_3$) δ 7.42-7.36 (m, 6H, H$_{ar}$), 7.34-7.29 (m, 10H, H$_{ar}$), 7.25-7.22 (m, 2H, H$_{ar}$), 7.12-7.06 (m, 3H, H$_{ar}$), 6.78-6.73 (m, H$_{ar}$), 6.67-6.64 (m, H$_{ar}$), 5.61-5.59 (m, 1H, CH), 2.29 (s, CH$_3$), 2.25 (s, CH$_3$). $^{13}$C NMR (125 MHz, CDCl$_3$) δ 154.35 (d, J=21.6 Hz), 131.35 (d, J=21.3 Hz), 143.93 (d, J=5.2 Hz), 143.25, 143.21, 143.11, 142.84, 137.06 (d, J=14.3 Hz), 136.84 (d, J=14.4 Hz), 136.53 (d, J=14.9 Hz), 133.43 (d, J=2.7 Hz), 132.87, 131.42 (d, J=8.8 Hz), 129.17, 129.11, 128.76, 128.61, 128.36 (d, J=2.2 Hz), 128.10, 127.77, 127.46 (d, J=12.4 Hz), 125.64, 125.52, 125.36, 124.06, 124.50, 124.28, 76.37, 76.15, 21.47. $^{31}$P NMR (203 MHz, CDCl$_3$) δ −50.95 & −51.49. HRMS (ESI) calculated [M+H]$^+$ for C$_{32}$H$_{27}$ClOP: 493.1483. found: 493.1480. FTIR (cm$^{-1}$) 3054.42, 1733, 1659, 1589, 1484, 1435, 1402, 1255, 1184, 1116, 1087, 1073, 1053, 1028, 1013, 997, 966, 933, 848, 822, 794, 748, 721, 691, 665, 633.

Example 32: Synthesis of 3-(4-Chlorophenyl)-5-fluoro-1,1,1-triphenyl-1,3-dihydro-1λ$^5$-benzo[c][1,2] oxaphosphole & 3-(4-Chlorophenyl)-6-fluoro-1,1,1-triphenyl-1,3-dihydro-1λ$^5$-benzo[c][1,2] oxaphosphole (4af & 4af')

Following the general procedure, treatment of 4-fluoro-2-(trimethylsilyl)phenyl trifluoromethanesulfonate 1a (0.189 g, 0.60 mmol) and 4-chlorobenzaldehyde 1b (0.105 g, 0.75 mmol) with triphenylphosphine 1c (0.131 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(4-chlorophenyl)-5-fluoro-1,1,1-triphenyl-1,3-dihydro-1λ$^5$-benzo[c] [1,2] oxaphosphole 4af and 3-(4-chlorophenyl)-6-fluoro-1,1,1-triphenyl-1,3-dihydro-1λ$^5$-benzo[c] [1,2]oxaphosphole 4af' as inseparable mixture of regioisomers in 3:1 ratio as a white solid (0.216 g, 87% yield, regioisomeric ratio was determined by $^1$H NMR analysis of crude reaction mixture).

R$_f$ (EtOAc): 0.53; $^1$H NMR (500 MHz, CDCl$_3$) δ 7.45-7.38 (m, 4H, H$_{ar}$), 7.37-7.34 (m, 11H, H$_{ar}$), 7.27 (d, J=8.3 Hz, 3H, H$_{ar}$), 7.12-7.08 (m, 2H, H$_{ar}$), 6.98-6.80 (m, 2H, H$_{ar}$), 5.56 (s, 1H, CH). $^{13}$C NMR (125 MHz, CDCl$_3$) δ 165.72 (d, J$_{C-F}$=256.2 Hz), 157.26 (dd, J$_1$=7.9 Hz, J$_2$=24.8 Hz), 143.58, 142.47, 142.28, 138.83-138.62 (m), 133.27, 131.41, 131.34, 129.05, 128.29, 127.59 (d, J=12.4 Hz), 123.37, 122.63-122.31 (m), 115.10 (dd, J$_1$=17.2 Hz, J$_2$=20.4 Hz), 111.66 (t, J=21.3 Hz), 76.00. $^{31}$P NMR (203 MHz, CDCl$_3$) δ −52.59. Representative Peaks of Minor Isomer: $^1$H NMR δ 7.22-7.14 (m), 6.56-6.50 (m), 5.51 (s). $^{13}$C NMR δ 149.33 (d, J=20.0 Hz), 143.34, 142.73, 133.21, 131.47, 129.19, 128.58, 128.38, 125.86-125.66 (m), 124.48, 119.80 (d, J=23.4 Hz), 75.64. $^{31}$P NMR δ −52.23. HRMS (ESI) calculated [M+H]$^+$ for C$_{31}$H$_{24}$ClFOP: 497.1232. found: 497.1232. FTIR (cm$^{-1}$) 3843, 3744, 3678, 3648, 3012, 2361, 1741, 1693, 1597, 1483, 1217, 1086, 1053, 955, 830, 742, 697, 636.

Example 33: Synthesis of 3-(4-Chlorophenyl)-1,1,1-tri-p-tolyl-1,3-dihydro-1λ⁵-benzo[c][1,2] oxaphosphole (4ag)

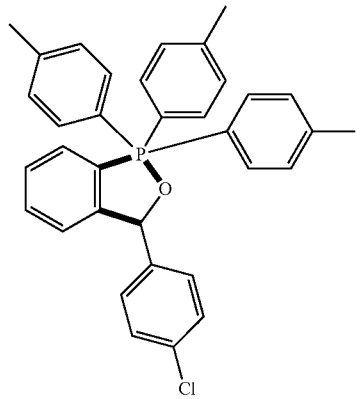

Following the general procedure, treatment of 2-(trimethylsilyl)phenyl trifluoromethanesulfonate 1a (0.179 g, 146 µL, 0.60 mmol) and 4-chlorobenzaldehyde 1b (0.105 g, 0.75 mmol) with tri-p-tolylphosphane 1c (0.152 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(4-chlorophenyl)-1,1,1-tri-p-tolyl-1,3-dihydro-1λ⁵-benzo[c][1,2]oxaphosphole 4ag as a white solid (0.193 g, 74% yield).

$R_f$(EtOAc): 0.30; ¹H NMR (400 MHz, CDCl₃) δ 7.47 (t, J=5.5 Hz, 1H, $H_{ar}$), 7.32-7.27 (m, 6H, $H_{ar}$), 7.24-7.20 (m, 4H, $H_{ar}$), 7.15-7.11 (m, 8H, $H_{ar}$), 6.90 (dd, =8.1 Hz, J₂=10.9 Hz, 1H, $H_{ar}$), 5.56 (s, 1H, CH), 2.39 (s, 9H, 3CH₃). ¹³C NMR (100 MHz, CDCl₃) δ 153.79 (d, J=20.1 Hz), 143.18, 140.10, 139.02, 137.97 (d, J=1.8 Hz), 136.49 (d, J=14.5 Hz), 132.77, 132.11, 131.59 (d, J=9.2 Hz), 129.38, 129.23, 128.23 (d, J=6.5 Hz), 128.07, 127.24 (d, J=14.1 Hz), 124.86 (d, J=15.1 Hz), 75.81, 21.36. ³¹P NMR (162 MHz, CDCl₃) δ −49.23 HRMS (ESI) calculated [M+H]⁺ for C₃₄H₃₁ClOP: 521.1796. found: 521.1797. FTIR (cm⁻¹) 3743, 3056, 2983, 1733, 1589, 1484, 1437, 1317, 1245, 1184, 1111, 1051, 846, 813, 745, 694. 662.

Example 34: Synthesis of 3-(4-Chlorophenyl)-1,1,1-tris(4-methoxyphenyl)-1,3-dihydro-1λ⁵-benzo[c][1,2] oxaphosphole (4ah)

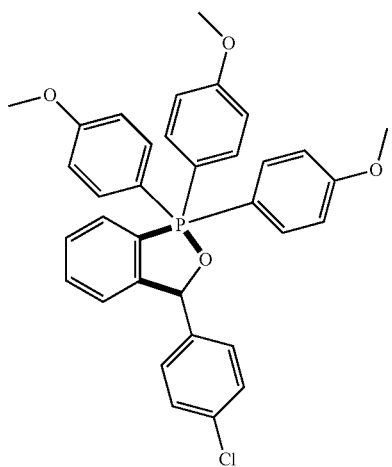

Following the general procedure, treatment of 2-(trimethylsilyl)phenyl trifluoromethanesulfonate 1a (0.179 g, 146 µL, 0.60 mmol) and 4-chlorobenzaldehyde 1b (0.105 g, 0.75 mmol) with tris(4-methoxyphenyl)phosphane 1c (0.176 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (EtOAc) of the crude reaction mixture using silica gel afforded 3-(4-chlorophenyl)-1,1,1-tris(4-methoxyphenyl)-1,3-dihydro-1λ⁵-benzo[c][1,2]oxaphosphole 4ah as a white solid (0.166 g, 58% yield).

$R_f$(EtOAc): 0.23; ¹H NMR (500 MHz, CDCl₃) δ 7.65 (t, J=7.0 Hz, 2H, $H_{ar}$), 7.35-7.31 (m, 7H, $H_{ar}$), 7.03-6.99 (m, 3H, $H_{ar}$), 6.92-6.91 (m, 6H, $H_{ar}$), 6.76 (bs, 2H, $H_{ar}$), 5.57 (s, 1H, CH), 3.82 (s, 9H, 3CH₃). ¹³C NMR (125 MHz, CDCl₃) δ 162.34 (d, J=8.8 Hz), 150.63, 141.46, 135.99 (d, J=13.3 Hz), 134.89 (d, J=7.3 Hz), 133.88, 132.73, 129.10, 128.40, 128.29, 128.04, 114.60, 73.86, 55.61. ³¹P NMR (203 MHz, CDCl₃) δ −40.79. HRMS (ESI) calculated [M+H]⁺ for C₃₄H₃₁ClO₄P: 569.1643. found: 569.1646. FTIR (cm⁻¹) 3894, 3678, 3619, 3018, 2362, 1741, 1693, 1596, 1464, 1264, 1267, 1217, 1110, 1027, 740, 667.

Example 35: Synthesis of 3-(4-Chlorophenyl)-1,1,1-tri-o-tolyl-1,3-dihydro-1λ⁵-benzo[c][1,2]oxaphosphole (4ai)

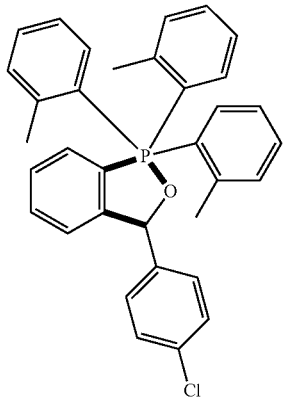

Following the general procedure, treatment of 2-(trimethylsilyl)phenyl trifluoromethanesulfonate 1a (0.179 g, 146 µL, 0.60 mmol) and 4-bromobenzaldehyde 1b (0.137 g, 0.75 mmol) with tri-o-tolylphosphane 1c (0.152 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (EtOAc) of the crude reaction mixture using silica gel afforded 3-(4-chlorophenyl)-1,1,1-tri-o-tolyl-1,3-dihydro-1λ⁵-benzo[c][1,2]oxaphosphole 4ai as a white solid (0.167 g, 64% yield).

$R_f$(EtOAc): 0.17; ¹H NMR (500 MHz, CDCl₃) δ 8.12-8.07 (m, 1H, $H_{ar}$), 8.03 (t, J=6.4 Hz, 1H, $H_{ar}$), 7.92-7.89 (m, 1H, $H_{ar}$), 7.72-7.69 (m, 2H, $H_{ar}$), 7.66-7.59 (m, 4H, $H_{ar}$), 7.48-7.46 (m, 2H, $H_{ar}$), 7.43-7.40 (m, 1H, $H_{ar}$), 7.34-7.30 (m, 2H, $H_{ar}$), 6.95-6.90 (m, 1H, $H_{ar}$), 6.86 (d, J=8.1 Hz, 2H, $H_{ar}$), 6.42 (d, J=7.9 Hz, 2H, $H_{ar}$), 5.58 (d, J=3.5 Hz, 1H, $H_{ar}$), 5.31 (d, J=4.0 Hz, 1H, CH), 1.82 (s, 6H, 2CH₃), 1.75 (s, 3H, CH₃). ¹³C NMR (125 MHz, CDCl₃) δ 148.45 (d, J=8.3 Hz), 144.25 (d, J=8.6 Hz), 143.68 (d, J=8.5 Hz), 142.98 (d, J=9.2 Hz), 139.12, 136.67 (d, J=12.6 Hz), 135.76-

135.68 (m), 135.55-135.49 (m), 135.39, 135.33, 134.76 (d, J=13.8 Hz), 134.39 (d, J=11.2 Hz), 133.92 (d, J=11.5 Hz), 133.56 (d, J=10.9 Hz), 133.25 (d, J=10.4 Hz), 133.07, 129.76 (d, J=13.0 Hz), 128.97 (d, J=13.3 Hz), 128.65, 128.59, 128.26, 128.06, 127.9 (d, J=12.9 Hz), 127.72, 121.89, 119.34, 116.33 (d, J=11.8 Hz), 115.84, 115.68 (d, J=10.8 Hz), 115.16, 114.73, 114.05, 72.19 (d, J=4.5 Hz), 23.19, 23.15, 22.86. $^{31}$P NMR (203 MHz, CDCl$_3$) δ 22.33 HRMS (ESI) calculated [M+H]$^+$ for C$_{34}$H$_{31}$ClOP: 521.1796. found: 521.1795. FTIR (cm$^{-1}$) 3893, 3843, 3678, 3619, 3019. 2362, 1836, 1741, 1693, 1646, 1516, 1464, 1215, 741, 668.

Example 36: Synthesis of 3-(4-Chlorophenyl)-1,1-diphenyl-1-(p-tolyl)-1,3-dihydro-1λ$^5$-benzo[c] [1,2] oxaphosphole (4aj)

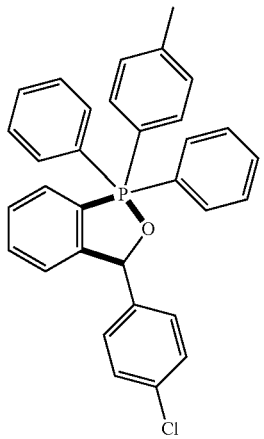

4aj

Following the general procedure, treatment of 2-(trimethylsilyl)phenyl trifluoromethanesulfonate 1a (0.179 g, 146 μL, 0.60 mmol) and 4-chlorobenzaldehyde 1b (0.105 g, 0.75 mmol) with diphenyl(p-tolyl)phosphane 1c (0.138 g, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 3-(4-chlorophenyl)-1,1-diphenyl-1-(p-tolyl)-1,3-dihydro-1λ$^5$-benzo[c][1,2]oxaphosphole 4aj as a white solid (0.198 g, 80% yield).

R$_f$ (EtOAc): 0.37; $^1$H NMR (400 MHz, CDCl$_3$) δ 7.49-7.45 (m, 1H, H$_{ar}$), 7.40-7.35 (m, 4H, H$_{ar}$), 7.32-7.28 (m, 8H, H$_{ar}$), 7.24-7.21 (m, 4H, H$_{ar}$), 7.14-7.12 (m, 2H, H$_{ar}$), 7.08 (d, J=8.2 Hz, 2H, H$_{ar}$), 6.88 (dd, J$_1$=8.4 Hz, J$_2$=11.0 Hz, 1H, H$_{ar}$), 5.59 (s, 1H, CH), 2.37 (s, 3H, CH$_3$). $^{13}$C NMR (100 MHz, CDCl$_3$) δ 153.84 (d, J=20.1 Hz), 142.99, 138.26 (d, J=2.2 Hz), 136.55 (d, J=14.4 Hz), 132.88, 132.28 (d, J=2.8 Hz), 131.85 (d, J=9.5 Hz), 131.47, 131.37 (d, J=2.9 Hz), 131.26, 129.18, 128.33, 128.27, 128.14, 127.49 (d, J=11.9 Hz), 127.30, 124.91 (d, J=15.1 Hz), 76.05, 21.38. $^{31}$P NMR (162 MHz, CDCl$_3$) δ −44.49. HRMS (ESI) calculated [M+H]$^+$ for C$_{32}$H$_{27}$ClOP: 493.1483. found: 493.1525. FTIR (cm$^{-1}$) 3861, 3649, 3062, 3006, 2319, 1740, 1693, 1596, 1437, 1399, 1259, 1222, 1185, 1017, 812, 743, 664.

Example 37: Synthesis of 1,1,1-Tributyl-3-(4-chlorophenyl)-1,3-dihydro-1λ$^5$-benzo[c] [1,2] oxaphosphole (4ak)

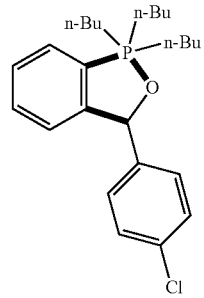

4ak

Following the general procedure, treatment of 2-(trimethylsilyl)phenyl trifluoromethanesulfonate 1a (0.179 g, 146 μL, 0.60 mmol) and 4-chlorobenzaldehyde 1b (0.105 g, 0.75 mmol) with tri-n-butylphosphine 1c (0.101 g, 125 μL, 0.50 mmol) in the presence of KF (0.070 g, 1.20 mmol) and 18-crown-6 (0.317 g, 1.20 mmol) in THF (3.0 mL) at −10° C. to rt for 12 h followed by flash column chromatography (Pet. ether/EtOAc=40/60) of the crude reaction mixture using silica gel afforded 1,1,1-tributyl-3-(4-chlorophenyl)-1,3-dihydro-1λ$^5$-benzo[c][1,2]oxaphosphole 4ak as a white solid (0.167 g, 79% yield).

R$_f$ (EtOAc): 0.21; $^1$H NMR (400 MHz, CDCl$_3$) δ 7.68 (dd, J$_1$=7.6 Hz, J$_2$=13.4 Hz, 1H, H$_{ar}$), 7.59-7.50 (m, 2H, H$_{ar}$), 7.25 (d, J=8.3 Hz, 2H, H$_{ar}$), 7.16 (d, J=8.5 Hz, 3H, H$_{ar}$), 6.05 (s, 1H, CH), 2.47-2.44 (m, 6H, 3CH$_2$), 1.50-1.21 (m, 12H, 6CH$_2$), 0.84 (t, J=6.5 Hz, 9H, 3CH$_3$). $^{13}$C NMR (100 MHz, CDCl$_3$) δ 143.38 (d, J=6.4 Hz), 141.37, 134.33 (d, J=8.8 Hz), 133.95 (d, J=2.2 Hz), 133.75, 131.52 (d, J=10.4 Hz), 128.85, 128.68 (d, J=12.7 Hz), 115.78, 115.00, 73.47 (d, J=1.8 Hz), 24.25 (d, J=4.1 Hz), 23.63 (d, J=16.3 Hz), 21.65 (d, J=50.3 Hz), 13.36. $^{31}$P NMR (162 MHz, CDCl$_3$) δ 32.97 HRMS (ESI) calculated [M+H]$^+$ for C$_{25}$H$_{37}$ClOP: 419.2265. found: 419.2265. FTIR (cm$^{-1}$) 3843, 3648, 3619, 3010, 2873, 2361, 1817, 1741, 1647, 1463, 1351, 1251, 1222, 1030, 949, 854, 742, 637.

The invention claimed is:
1. A compound selected from
3-(4-Chlorophenyl)-1,1,1-triphenyl-1,3-dihydro-1λ$^5$-benzo[c][1,2]oxaphosphole (4a),

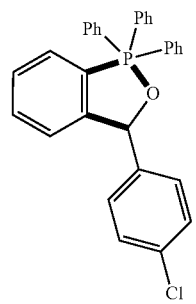

4a 3-(4-Methoxyphenyl)-1,1,1-triphenyl-1,3-dihydro-1λ$^5$-benzo[c][1,2]oxaphosphole (4b),

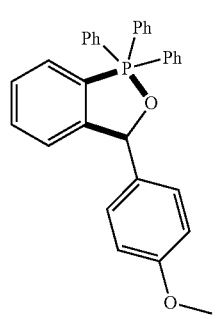

1,1,1-Triphenyl-3-(p-tolyl)-1,3-dihydro-1λ$^5$-benzo[c][1,2]oxaphosphole (4c),

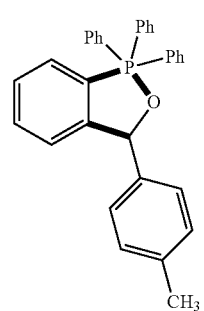

3-(4-Bromophenyl)-1,1,1-triphenyl-1,3-dihydro-1λ$^5$-benzo[c][1,2]oxaphosphole (4d),

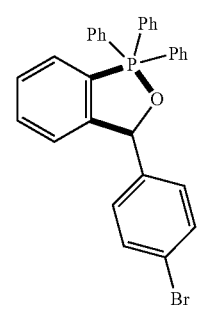

1,1,1,3-Tetraphenyl-1,3-dihydro-1λ$^5$-benzo[c][1,2]oxaphosphole (4e),

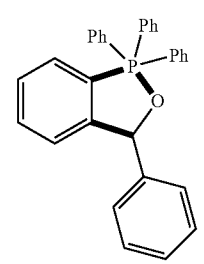

3-(4-Fluorophenyl)-1,1,1-triphenyl-1,3-dihydro-1λ$^3$-benzo[c][1,2]oxaphosphole (4f),

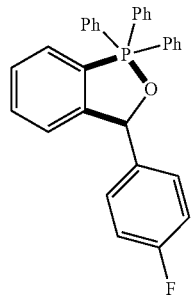

1,1,1-Triphenyl-3-(4-(trifluoromethyl)phenyl)-1,3-dihydro-1λ$^5$-benzo[c][1,2]oxaphosphole (4g),

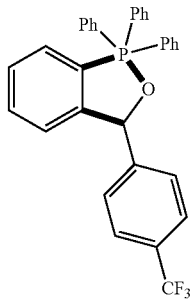

Methyl-4-(1,1,1-triphenyl-1,3-dihydro-1λ$^5$-benzo[c][1,2]oxaphosphol-3-yl) benzoate (4h),

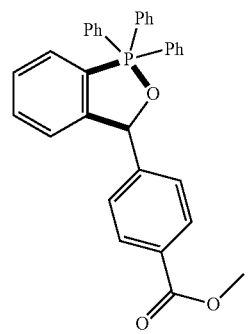

4-(1,1,1-Triphenyl-1,3-dihydro-1λ⁵-benzo[c][1,2]oxa-phosphol-3-yl)benzonitrile (4i),

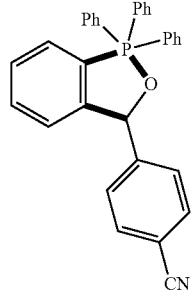

3-(3-Methoxyphenyl)-1,1,1-triphenyl-1,3-dihydro-1λ⁵-benzo[c][1,2]oxaphosphole (4j),

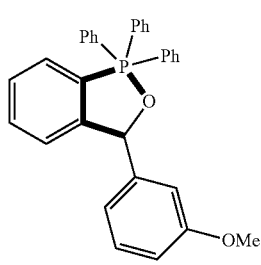

3-(3-Bromophenyl)-1,1,1-triphenyl-1,3-dihydro-1λ⁵-benzo[c][1,2]oxaphosphole (4k),

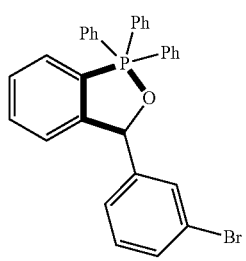

3-(3-Nitrophenyl)-1,1,1-triphenyl-1,3-dihydro-1λ⁵-benzo[c][1,2]oxaphosphole (4l),

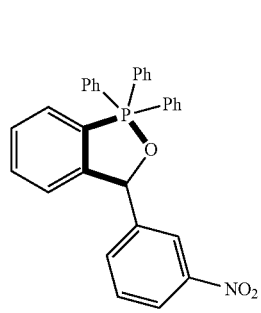

1,1,1-Triphenyl-3-(o-tolyl)-1,3-dihydro-1λ⁵-benzo[c][1,2]oxaphosphole (4m),

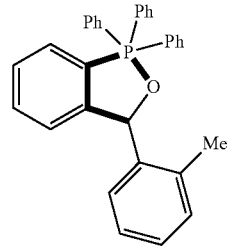

3-(2-Fluorophenyl)-1,1,1-triphenyl-1,3-dihydro-1λ⁵-benzo[c][1,2]oxaphosphole (4n),

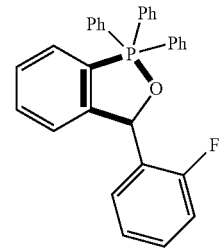

3-(3,4-Dichlorophenyl)-1,1,1-triphenyl-1,3-dihydro-1λ⁵-benzo[c][1,2]oxaphosphole (4o),

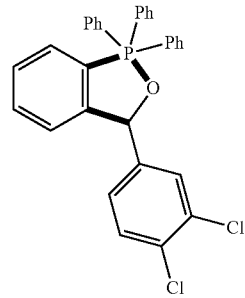

3-Mesityl-1,1,1-triphenyl-1,3-dihydro-1λ⁵-benzo[c][1,2]oxaphosphole (4p),

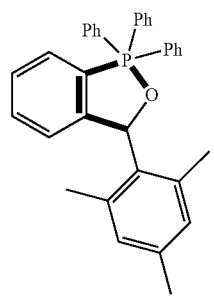

3-(Naphthalen-2-yl)-1,1,1-triphenyl-1,3-dihydro-1λ⁵-benzo[c][1,2]oxaphosphole (4q),

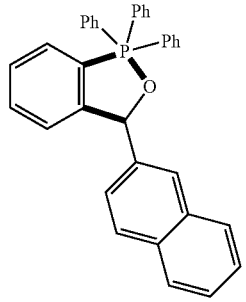

1,1,1-Triphenyl-3-(pyren-4-yl)-1,3-dihydro-1λ⁵-benzo[c][1,2]oxaphosphole (4r),

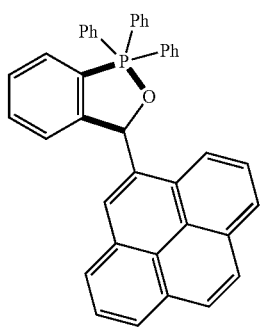

3-(Benzofuran-2-yl)-1,1,1-triphenyl-1,3-dihydro-1λ⁵-benzo[c][1,2]oxaphosphole (4s),

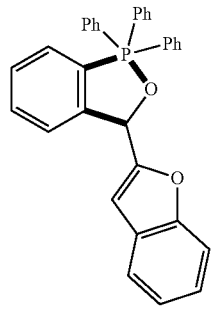

1,1,1-Triphenyl-3-(thiophen-2-yl)-1,3-dihydro-1λ⁵-benzo[c][1,2]oxaphosphole (4t),

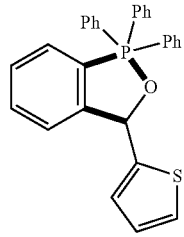

3-Cyclohexyl-1,1,1-triphenyl-1,3-dihydro-1λ⁵-benzo[c][1,2]oxaphosphole (4u),

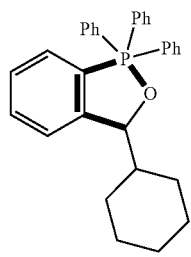

3-Nonyl-1,1,1-triphenyl-1,3-dihydro-1λ⁵-benzo[c][1,2]oxaphosphole (4v),

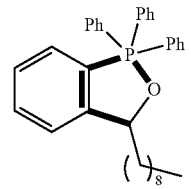

1,1,1-Triphenyl-3-vinyl-1,3-dihydro-1λ⁵-benzo[c][1,2]oxaphosphole (4w),

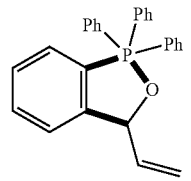

1,1,1-Triphenyl-3-styryl-1,3-dihydro-1λ⁵-benzo[c][1,2]oxaphosphole (4x),

53

3-(4-Methoxystyryl)-1,1,1-triphenyl-1,3-dihydro-1λ$^5$-benzo[c][1,2]oxaphosphole (4y),

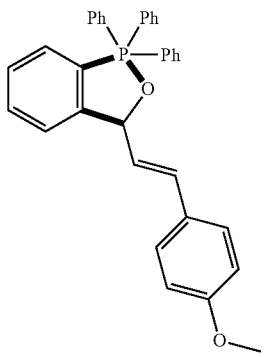
4y 3-(4-Chlorophenyl)-5,6-dimethyl-1,1,1-triphenyl-1,3-dihydro-1λ$^5$benzo[c][1,2]oxaphosphole (4z),

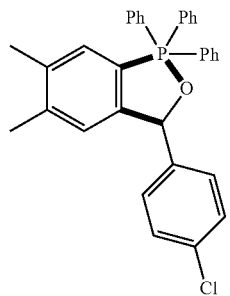
4z 3-(4-Chlorophenyl)-5,6-difluoro-1,1,1-triphenyl-1,3-dihydro-1λ$^5$-benzo[c][1,2]oxaphosphole (4aa),

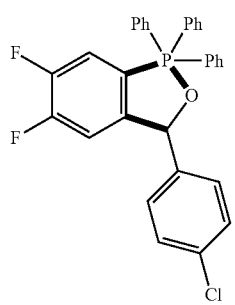
4aa

54

3-(4-Chlorophenyl)-1,1,1-triphenyl-1,3-dihydro-1λ$^5$-[1,3]dioxolo[4',5':4,5]benzo[1,2-c][1,2]oxaphosphole (4ab),

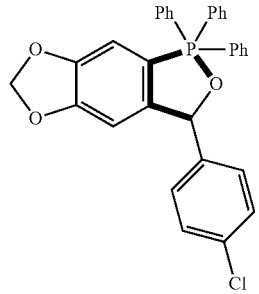
4ab 3-(4-Chlorophenyl)-1,1,1-triphenyl-3,5,6,7-tetrahydro-1H-1λ$^5$-indeno[5,6-c][1,2]oxaphosphole (4ac),

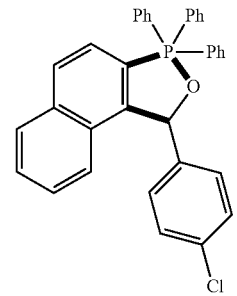
4ac 1-(4-Chlorophenyl)-3,3,3-triphenyl-1,3-dihydro-3λ$^3$-naphtho[2,1-c][1,2]oxaphosphole (4ad),

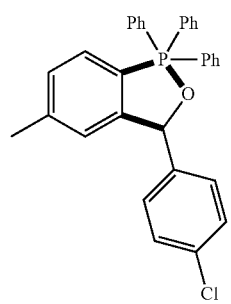
4ad 3-(4-Chlorophenyl)-5-methyl-1,1,1-triphenyl-1,3-dihydro-1λ$^5$-benzo[c][1,2]oxaphosphole (4ae)

4ae 3-(4-Chlorophenyl)-6-methyl-1,1,1-triphenyl-1,3-di-
hydro-1λ⁵-benzo[c][1,2]oxaphosphole (4ae')

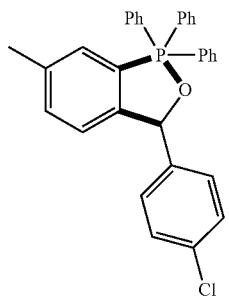

3-(4-Chlorophenyl)-5-fluoro-1,1,1-triphenyl-1,3-di-
hydro-1λ⁵-benzo[c][1,2]oxaphosphole (4af),

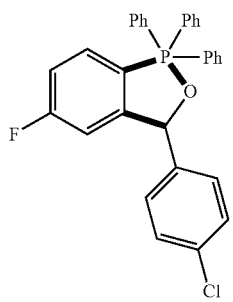

3-(4-Chlorophenyl)-6-fluoro-1,1,1-triphenyl-1,3-di-
hydro-1λ⁵-benzo[c][1,2]oxaphosphole (4af'),

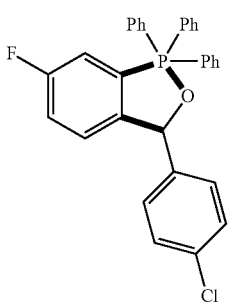

3-(4-Chlorophenyl)-1,1,1-tri-p-tolyl-1,3-dihydro-1λ⁵-
benzo[c][1,2]oxaphosphole (4ag),

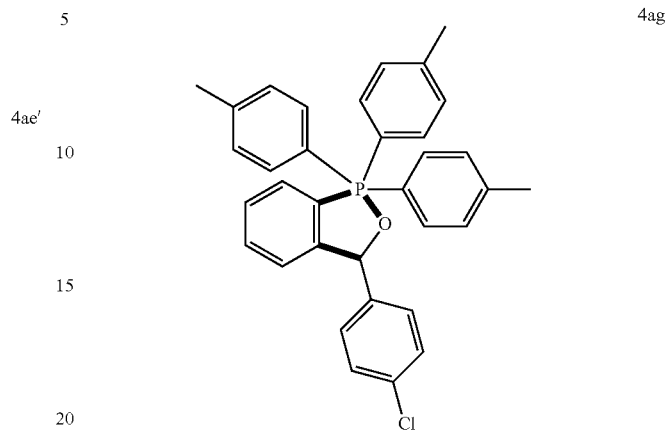

3-(4-Chlorophenyl)-1,1,1-tris(4-methoxyphenyl)-1,3-di-
hydro-1λ⁵-benzo[c][1,2]oxaphosphole (4ah),

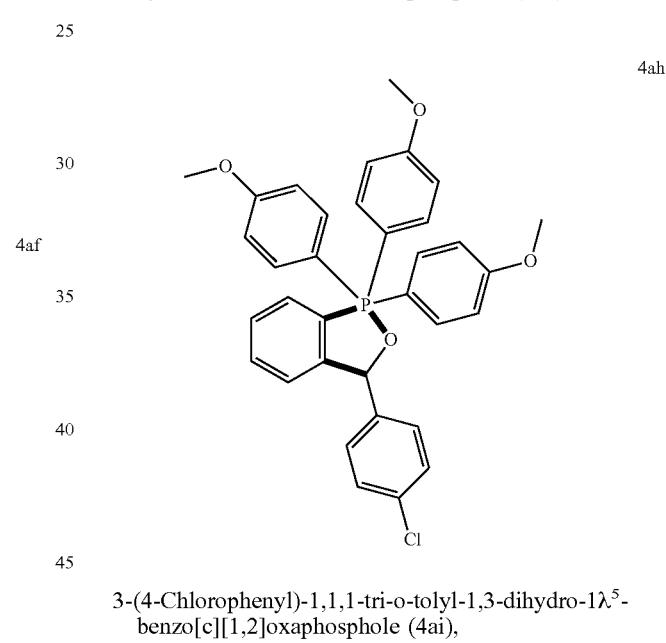

3-(4-Chlorophenyl)-1,1,1-tri-o-tolyl-1,3-dihydro-1λ⁵-
benzo[c][1,2]oxaphosphole (4ai),

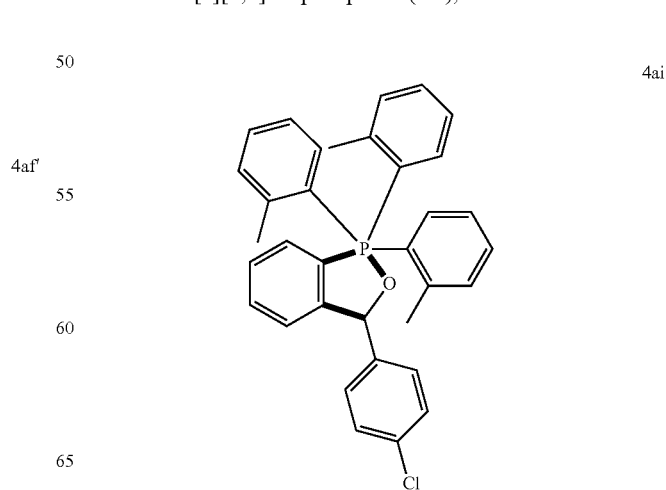

3-(4-Chlorophenyl)-1,1-diphenyl-1-(p-tolyl)-1,3-di-hydro-1λ⁵-benzo[c][1,2]oxaphosphole (4aj)

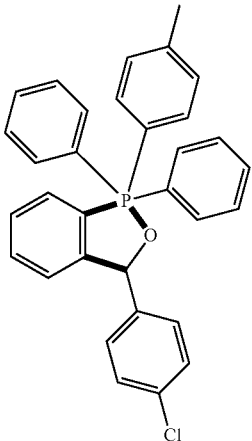

4aj and 1,1,1-Tributyl-3-(4-chlorophenyl)-1,3-dihydro-1λ⁵-benzo[c][1,2]oxaphosphole (4ak)

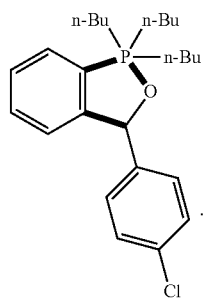

4ak

2. A process for preparing a compound of claim 1, wherein the process comprises the steps of:
a) cooling a reaction mixture of 18-crown-6, KF and a phosphine precursor in THF at −10° C. to −0° C. followed by stirring for 5-10 minutes;
b) adding an aryne precursor to the reaction mixture of step (a) followed by continued stirring for an additional 5-10 minutes at −10° C. to 0° C.;
c) adding an aldehyde to the reaction mixture of step (b) and continued stirring from −10° C. to room temperature for 12 h-15 h to obtain a compounds of claim 1, wherein room temperature is from 25-35° C.

3. The process as claimed in claim 2, wherein the process is carried out under an argon atmosphere.

4. The process as claimed in claim 2, wherein the aryne precursors are selected from trimethylsilyl triflates optionally substituted with one or two substituents each of which is independently selected from alkyl, halogen, alkoxy, haloalkyl, cyano, nitro, hydroxy, aryl, naphthyl, phenanthryl and may optionally form carbocyclic ring or heterocyclic ring containing one or more heteroatoms selected from the group consisting of: O, N.

5. The process as claimed in claim 4, wherein the aryne precursors are selected from 2-(trimethylsilyl)phenyl trifluoromethanesulfonate, 4,5-dimethyl-2-(trimethylsilyl)phenyl trifluoromethanesulfonate, 4,5-difluoro-2-(trimethylsilyl) phenyl trifluoromethanesulfonate, 6-(trimethylsilyl) benzo[d][1,3]dioxol-5-yl trifluoromethanesulfonate, 6-(trimethylsilyl)-2,3-dihydro-1H-inden-5-yl trifluoromethanesulfonate, 2-(trimethylsilyl)naphthalen-1-yl trifluoromethanesulfonate, 5-methyl-2-(trimethylsilyl)phenyl trifluoromethanesulfonate, 4-fluoro-2-(trimethylsilyl)phenyl trifluoromethanesulfonate.

6. The process as claimed in claim 2, wherein the aldehydes are selected from aromatic aldehydes, aliphatic aldehydes, heterocyclic aldehydes; and α,β-unsaturated aldehydes.

7. The process as claimed in claim 6, wherein the aldehydes are selected from benzaldehyde, 4-chlorobenzaldehyde, 4-methoxybenzaldehyde, 4-methylbenzaldehyde, 4-bromobenzaldehyde, 4-fluorobenzaldehyde, 4-(trifluoromethyl)benzaldehyde, methyl 4-formylbenzoate, 4-formylbenzonitrile, 3-methoxybenzaldehyde, 3-bromobenzaldehyde, 3-nitrobenzaldehyde, 2-methylbenzaldehyde, 2-fluorobenzaldehyde, 3,4-dichlorobenzaldehyde, 2,4,6-trimethylbenzaldehyde, 2-naphthaldehyde, pyrene-4-carbaldehyde, benzofuran-2-carbaldehyde, thiophene-2-carbaldehyde, cyclohexanecarbaldehyde, decanal, acrylaldehyde, trans cinnamaldehyde, (E)-3-(4-methoxyphenyl)acrylaldehyde.

8. The process as claimed in claim 2, wherein the phosphine precursors are selected from tri-p-tolylphosphane, tris(4-methoxyphenyl)phosphane, tri-o-tolylphosphane, diphenyl (p-tolyl)phosphane, tri-n-butylphosphine.

9. The process as claimed in claim 2, wherein a yield of the compounds of claim 1 is 55-95%.

* * * * *